United States Patent
Watanabe et al.

(10) Patent No.: US 11,510,558 B2
(45) Date of Patent: Nov. 29, 2022

(54) ENDOSCOPE OBSERVATION METHOD AND ENDOSCOPE APPARATUS

(71) Applicant: OLYMPUS CORPORATION, Tokyo (JP)

(72) Inventors: Yoshihiko Watanabe, Yokohama (JP); Takeshi Ito, Ino (JP)

(73) Assignee: OLYMPUS CORPORATION, Tokyo (JP)

( * ) Notice: Subject to any disclaimer, the term of this patent is extended or adjusted under 35 U.S.C. 154(b) by 1160 days.

(21) Appl. No.: 16/047,074

(22) Filed: Jul. 27, 2018

(65) Prior Publication Data

US 2018/0368670 A1    Dec. 27, 2018

Related U.S. Application Data

(63) Continuation of application No. PCT/JP2016/052332, filed on Jan. 27, 2016.

(51) Int. Cl.
*A61B 5/00* (2006.01)
*A61B 1/00* (2006.01)
(Continued)

(52) U.S. Cl.
CPC ........ *A61B 1/0638* (2013.01); *A61B 1/00009* (2013.01); *A61B 5/0075* (2013.01);
(Continued)

(58) Field of Classification Search
None
See application file for complete search history.

(56) References Cited

U.S. PATENT DOCUMENTS

| | | |
|---|---|---|
| 2009/0262225 A1 | 10/2009 | Yamaguchi et al. |
| 2014/0031628 A1 | 1/2014 | Kaku |

(Continued)

FOREIGN PATENT DOCUMENTS

| | | |
|---|---|---|
| CN | 103654700 A | 3/2014 |
| JP | 2009-253419 A | 10/2009 |

(Continued)

OTHER PUBLICATIONS

Arimoto, "Multispectral Polarization Imaging for Observing Blood Oxygen Saturation in Skin Tissue" Applied Spectroscopy vol. 60, No. 4, 2006 pp. 459-464 (Year: 2006).*

(Continued)

*Primary Examiner* — Colin T. Sakamoto
(74) *Attorney, Agent, or Firm* — Scully, Scott, Murphy & Presser, P.C.

(57) ABSTRACT

An endoscope observation method includes irradiating first and second narrowband light to an observation object. The first and second narrowband light have wavelengths at which absorbances of first and second characteristic substances related to a predetermined state of the observation object and contained in the observation object are mutually different. The method also includes performing imaging by use of reflected light of the first and second narrowband light from the observation object to obtain first and second image data, and forming a characteristic substance presence image regarding the presence of the first and second characteristic substance, on the basis of characteristic amounts of the first and second characteristic substances contained in the first and second image data.

11 Claims, 15 Drawing Sheets

(51) Int. Cl.
  *A61B 1/06* (2006.01)
  *G02B 23/24* (2006.01)
  *A61B 1/05* (2006.01)
  *A61B 1/045* (2006.01)

(52) U.S. Cl.
  CPC ........ *A61B 5/0084* (2013.01); *G02B 23/2461* (2013.01); *A61B 1/00186* (2013.01); *A61B 1/045* (2013.01); *A61B 1/05* (2013.01); *A61B 1/0684* (2013.01)

(56) References Cited

U.S. PATENT DOCUMENTS

| | | | |
|---|---|---|---|
| 2015/0022647 A1 | 1/2015 | Takei et al. | |
| 2015/0182118 A1 | 7/2015 | Bradbury et al. | |
| 2015/0374218 A1 | 12/2015 | Nishio et al. | |
| 2017/0086648 A1* | 3/2017 | Kamee | A61B 1/0646 |

FOREIGN PATENT DOCUMENTS

| | | |
|---|---|---|
| JP | 2012-147928 A | 8/2012 |
| JP | 2014-023591 A | 2/2014 |
| JP | 2014-171511 A | 9/2014 |
| JP | 5698878 B2 | 4/2015 |
| JP | 2015-091467 A | 5/2015 |
| JP | 2016-002133 A | 1/2016 |
| WO | WO-2015190255 A1 * | 12/2015 ......... A61B 1/00009 |

OTHER PUBLICATIONS

Huang "Multispectral Imaging of Skin Oxygenation" Dissertation, the Graduate School of the Ohio State University, 2013 (Year: 2013).*
Lu et al., "Estimation of Tissue Optical Parameters with Hyperspectral Imaging and Spectral Unmixing" Proc. SPIE 9417, Medical Imaging 2015: Biomedical Applications in Molecular, Structural, and Functional Imaging, 94170Q (Mar. 17, 2015) (Year: 2015).*
International Search Report dated Apr. 26, 2016 issued in PCT/JP2016/052332.
Chinese Office Action dated Nov. 4, 2019 in Chinese Patent Application No. 201680080415.1.
English translation of International Preliminary Report on Patentability dated Aug. 9, 2018 together with the Written Opinion received in related International Application No. PCT/JP2016/052332.
Japanese Office Action dated Sep. 3, 2019 in Japanese Patent Application No. 2017-563456.

* cited by examiner

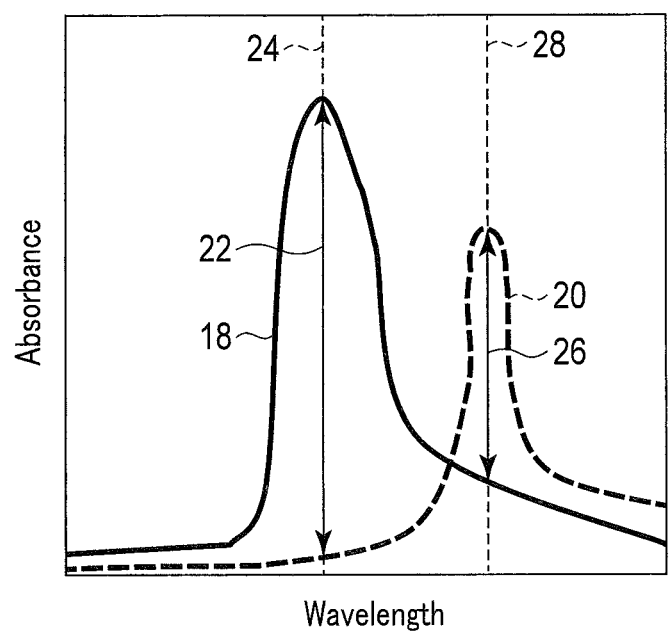
F I G. 4
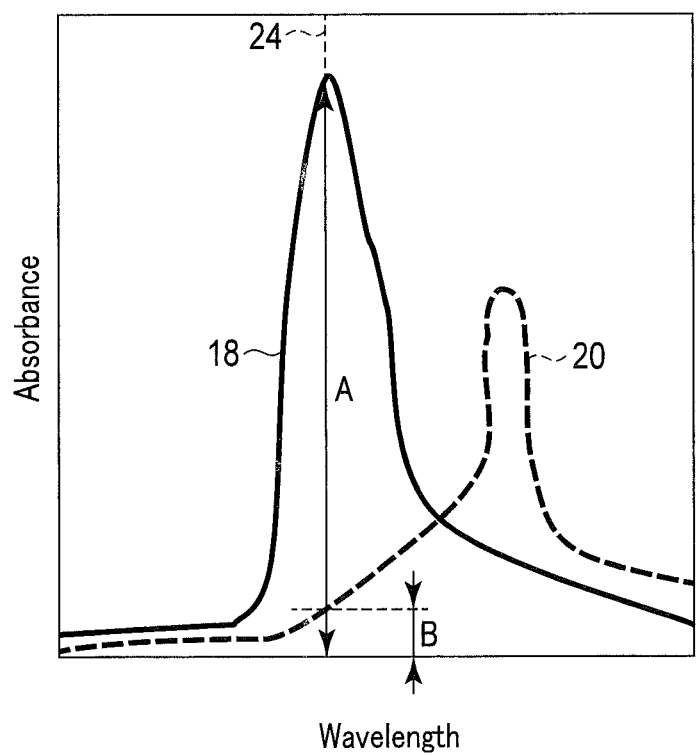
F I G. 5

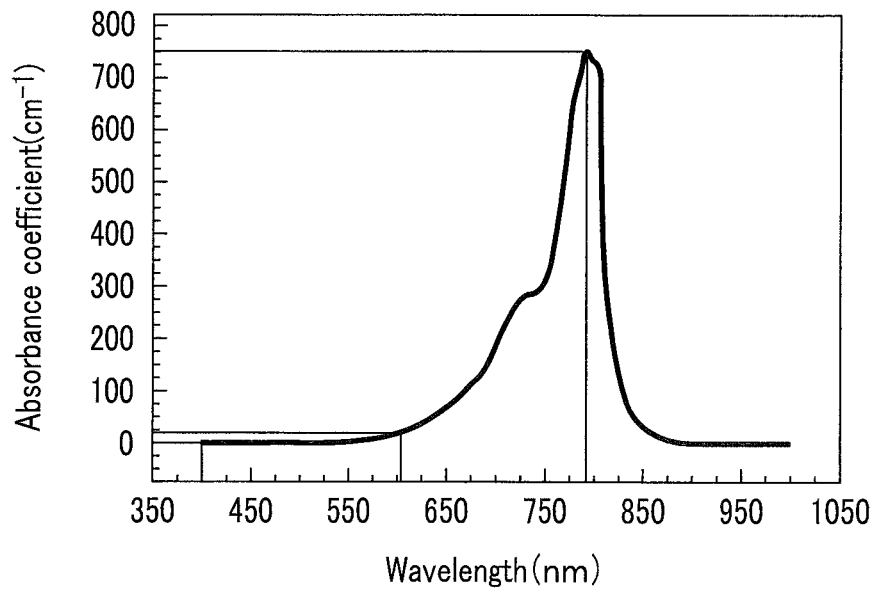
F I G. 8
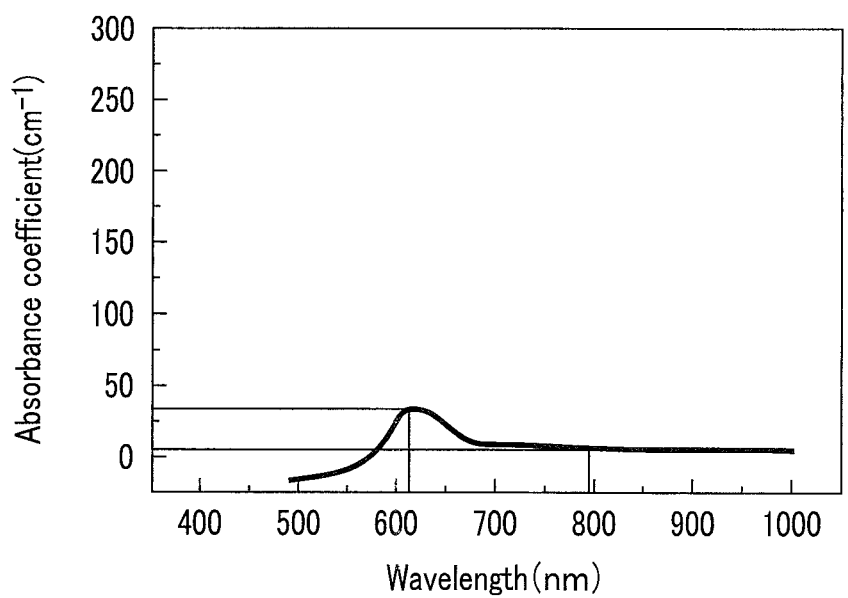
F I G. 9

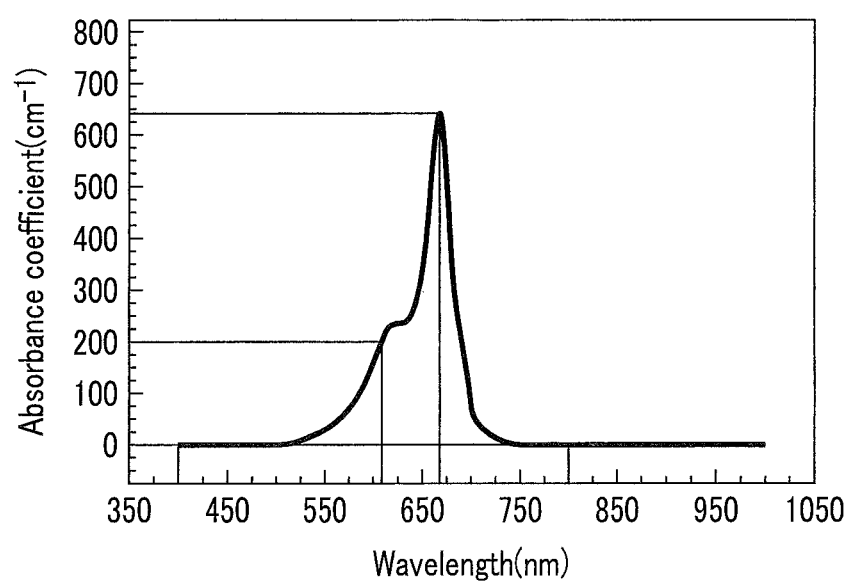
F I G. 15

ENDOSCOPE OBSERVATION METHOD AND ENDOSCOPE APPARATUS

CROSS-REFERENCE TO RELATED APPLICATIONS

This application is a Continuation Application of PCT Application No. PCT/JP2016/052332, filed Jan. 27, 2016, the entire contents of which are incorporated herein by reference.

BACKGROUND OF THE INVENTION

1. Field of the Invention

The present invention relates to an endoscope observation method to observe a subject, and an endoscope apparatus.

2. Description of the Related Art

At present, finding of a noticeable region in a subject, e.g., a lesion in a body cavity by an endoscope has been performed as follows. That is, a rough observation is firstly performed by screening with white light. On the basis of results of the observation, specific light such as NBI is irradiated to an area where a disease is suspected, to detect a characteristic substance closely related to the lesion, e.g., hemoglobin or the like in the blood, as disclosed in Jpn. Pat. Appln. KOKAI Publication No. 2015-91467. The thus obtained detection results of the characteristic substance are useful for the finding of the lesion of cancer, tumor or the like.

BRIEF SUMMARY OF THE INVENTION

An endoscope observation method includes irradiating, to an observation object, first narrowband light and second narrowband light having wavelengths at which absorbances of a first characteristic substance and a second characteristic substance related to a predetermined state of the observation object and contained in the observation object are mutually different, performing imaging by use of reflected light of the first narrowband light from the observation object to obtain first image data, and by use of reflected light of the second narrowband light to obtain second image data, and forming a characteristic substance presence image regarding presence of the first characteristic substance and the second characteristic substance, on the basis of a characteristic amount of the first characteristic substance contained in the first image data and a characteristic amount of the second characteristic substance contained in the second image data.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a view showing absorption spectra of a first characteristic substance and a second characteristic substance to explain an example of a selection method of first narrowband light and second narrowband light;

FIG. 5 is a view showing absorption spectra of a first characteristic substance and a second characteristic substance to explain another example of the selection method of the first narrowband light and the second narrowband light;

FIG. 8 is a view showing an absorption spectrum of indocyanine green as an example of the second characteristic substance;

FIG. 9 is a view showing an absorption spectrum of indigo carmine as another example of the first characteristic substance;

FIG. 15 is a view showing an absorption spectrum of methylene blue as still another example of the first characteristic substance;

DETAILED DESCRIPTION OF THE INVENTION

Hereinafter, an embodiment to perform the present invention will be described with reference to the accompanying drawings.

It is to be noted that an endoscope referred to in this specification should not be limited to an endoscope for medical use (an upper gastrointestinal tract endoscope, a large intestine endoscope, an ultrasonic endoscope, a cystoscope, a pyeloscope, a bronchoscope, or the like) and an endoscope for industrial use, and the endoscope indicates a general instrument having an insertion section to be inserted into a subject (e.g., a body cavity (a lumen)).

Hereinafter, as an example of the endoscope, an endoscope for medical use will be described.

Figure 1A:
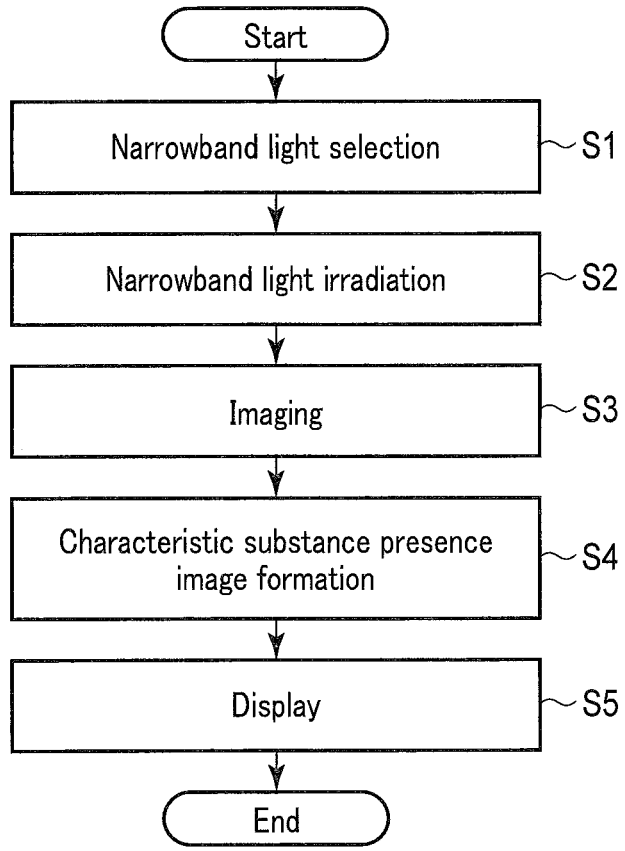
FIG. 1A is a flowchart to explain the outline of an endoscope observation method according to an embodiment of the present invention.

First, the outline of an endoscope observation method according to an embodiment of the present invention will be described with reference to a flowchart shown in FIG. 1A.

Figure 1B:
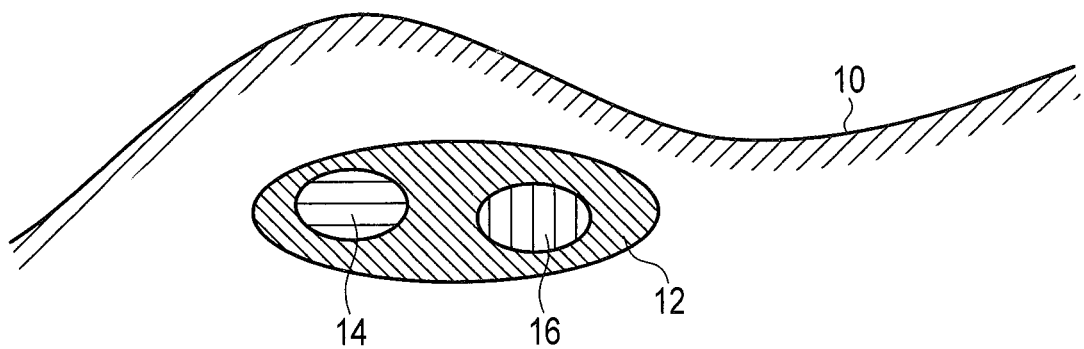
FIG. 1B is a schematic view to explain a noticeable region in a subject.

That is, in the endoscope observation method according to the present embodiment, narrowband light is first selected (Step S1). As shown in FIG. 1B, a subject 10 that is an intended observation object might contain a noticeable region 12, e.g., a lesion in a body cavity, and such a noticeable region 12 contains a first characteristic substance 14 and a second characteristic substance 16. Then, first narrowband light contained in a first wavelength range and second narrowband light contained in a second wavelength range are selected, the first narrowband light and second narrowband light having wavelengths at which absorbances of the first characteristic substance 14 and the second characteristic substance 16 are mutually different. It is to be noted that the selection method of the first and second narrowband light will be described in detail hereinafter.

Next, the thus selected first narrowband light and second narrowband light are irradiated from an irradiating section arranged at a distal end of the insertion section of the endoscope to the subject 10 (Step S2). Then, in an imaging section similarly arranged at the distal end of the insertion section of the endoscope, imaging is performed by use of reflected light of the first narrowband light and reflected light of the second narrowband light from the subject 10 (Step S3).

Next, on the basis of image data obtained by the imaging, a characteristic substance presence image that indicates the presence of the first characteristic substance and the second characteristic substance is formed (Step S4). Then, the thus formed characteristic substance presence image is displayed on a display such as a monitor connected to a main section (a video processor) with which the endoscope is connected (Step S5).

Thus, the narrowband light are irradiated to the subject 10, for the characteristic substances 14, 16 closely related to the noticeable region 12 that is the intended observation object, the narrowband light having the wavelengths at which the absorbances of the respective characteristic substances are mutually different, so that the characteristic substances 14, 16 related to the noticeable region 12 can be detected. That is, the observation object has been heretofore discovered from detection results of a single characteristic substance, but in the present embodiment, the observation object is discovered from detection results of the characteristic substances, and hence it is possible to improve discovery precision of the observation object.

In this connection, it is desirable that the first characteristic substance 14 and the second characteristic substance 16 are different kinds of dyes suitable for different use applications. For example, the first characteristic substance 14 is hemoglobin, which is a blood vessel emphasizing substance to emphasize blood vessels, and the second characteristic substance 16 is indigo carmine, which is a structure emphasizing substance to emphasize a structure or a bit pattern of cells.

The first characteristic substance 14 and the second characteristic substance 16 are suitably dyes that are known as markers for cancers. The employment of various kinds of markers for the cancers exhibits effects to heighten a detection sensitivity and the prevention of cancer detection errors.

Hereinafter, the endoscope observation method according to the present embodiment will be described in detail.

Figure 2:
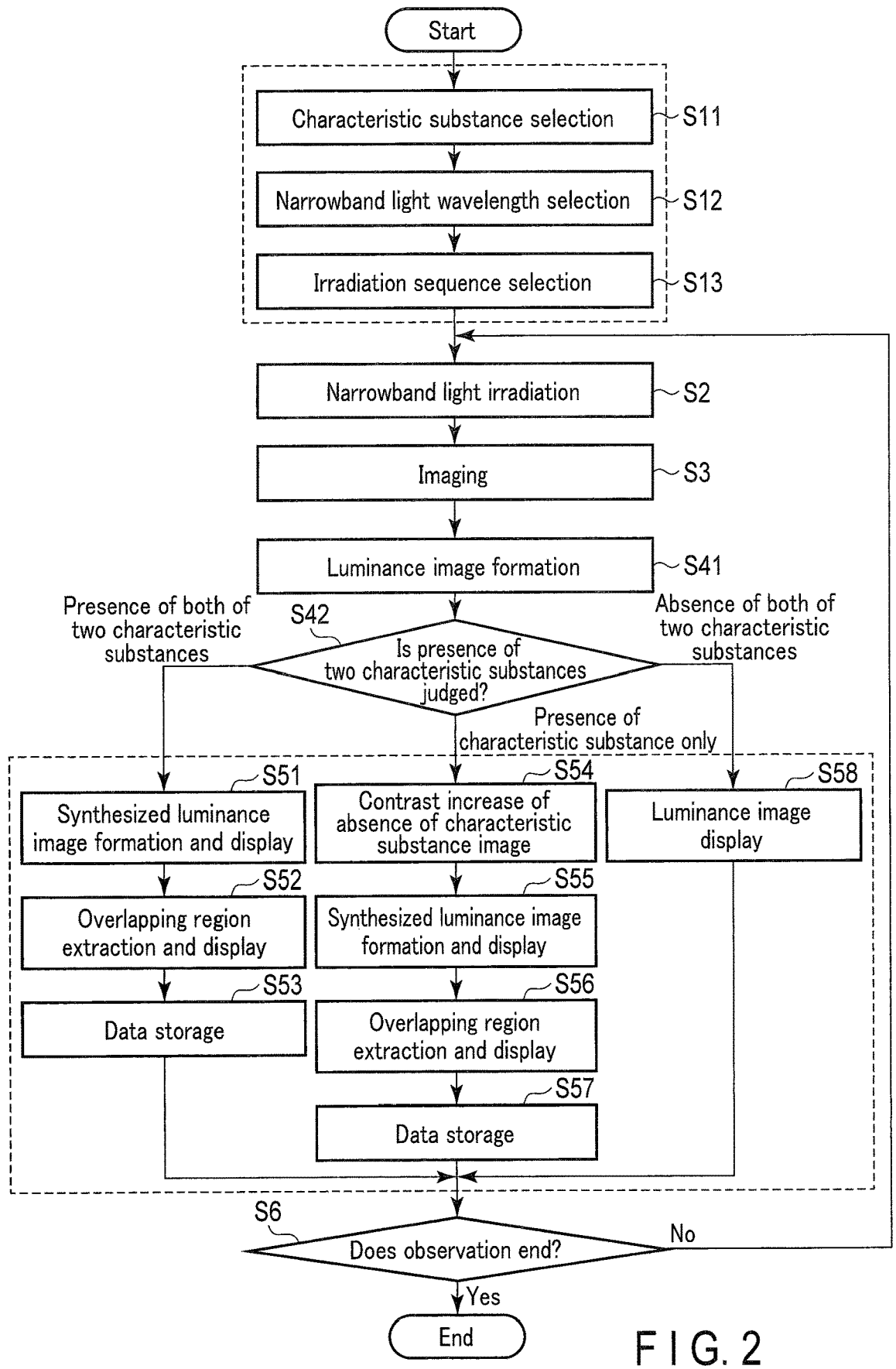
FIG. 2 is a flowchart to explain the detail of an endoscope observation method according to an embodiment of the present invention.

As shown by a flowchart in FIG. 2, Step S1 to select the two kinds of narrowband light includes a characteristic substance selecting step (Step S11), a narrowband light wavelength selecting step (Step S12), and an irradiation sequence selecting step (Step S13).

For example, the characteristic substance selecting step of Step S11 is a step to select the first characteristic substance 14 and the second characteristic substance 16. The selection of the first and second characteristic substances 14 and 16 can be performed, for example, by optional selection of an observer from a list of characteristic substances. Here, as to the list of the characteristic substances, for example, a combination of the two characteristic substances related to a tumor or a lesion such as a combination of hemoglobin, which is a dye to emphasize a structure of a blood vessel component closely related to the tumor, and indocyanine green (hereinafter abbreviated as ICG), which is a dye to emphasize a structure of a bit pattern or the like are previously listed up.

Furthermore, a combination of characteristic substances may be selected in accordance with a kind of the noticeable region 12. Alternatively, like the above list of the characteristic substances, a list of recommended combinations in accordance with a kind of the noticeable region 12 may be previously prepared, and the first and second characteristic substances 14, 16 may be selected from the list.

It is noted that the "selection" in each of the characteristic substance selecting step, the narrowband light wavelength selecting step and the irradiation sequence selecting step of the above steps S11 to S13 indicates the "selection" in a broad sense. That is, the "selection" covers a case of selecting among plural choices, and a case of a previously determined choice owing to no choice.

Therefore, for example, in a case of an exclusive endoscope in which a kind of the noticeable region 12 is specified, a desired characteristic substance is selected from a list of recommended combinations corresponding to the specified kind of the noticeable region 12.

The narrowband light wavelength selecting step of Step S12 is a step to select the first narrowband light and the second narrowband light in accordance with the selected first and second characteristic substances 14, 16. The two kinds of narrowband light (the first narrowband light and the second narrowband light) having mutually different wavelengths that can detect the two mutually different characteristic substances (the first characteristic substance 14 and the second characteristic substance 16) are selected in the following manner.

That is, the first narrowband light and the second narrowband light are selected so that a difference between absorbances of the first characteristic substance 14 and the second characteristic substance 16 at the respective wavelengths is a predetermined value or more.

Specifically, the first narrowband light containing a wavelength at which a difference between the absorbances of the first characteristic substance 14 and the second characteristic substance 16 at the respective wavelengths is a largest value or a maximum value, and the second narrowband light containing a wavelength at which the difference is a smallest value or a minimum value are selected as the first narrowband light and the second narrowband light.

Figure 3:
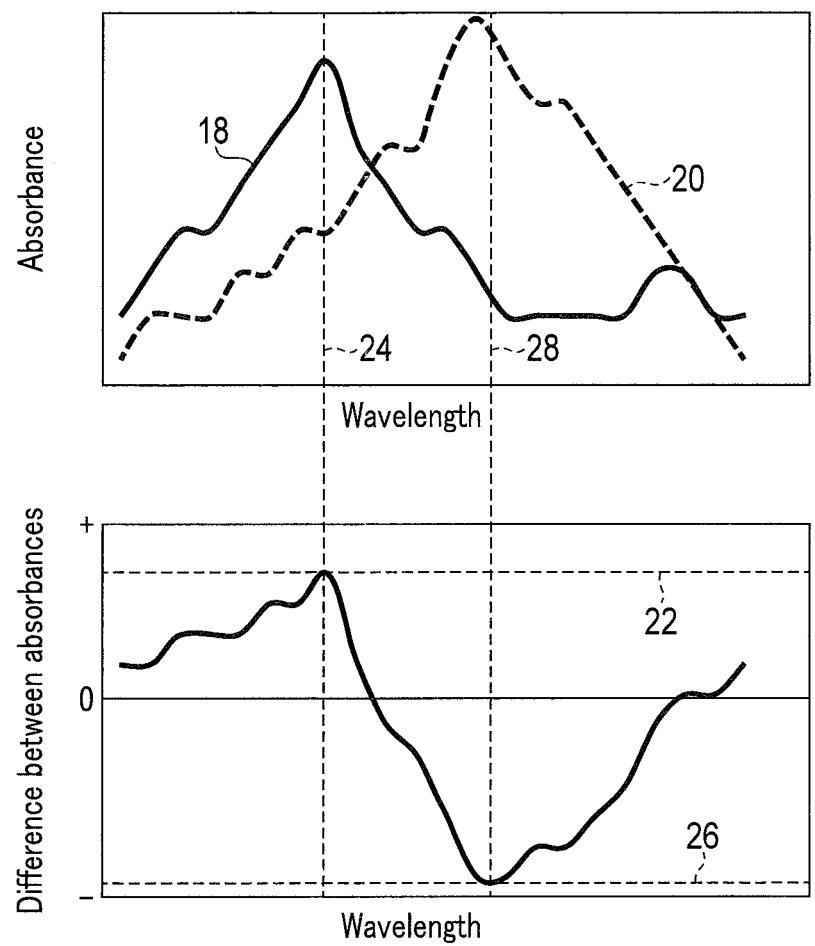
FIG. 3 is a view to explain a difference between absorbances of two characteristic substances.

It is to be noted that the difference between the absorbances is a value obtained by subtracting the absorbance of the second characteristic substance 16 from that of the first characteristic substance 14. Therefore, as understood from an optical absorption spectrum 18 of the first characteristic substance and an optical absorption spectrum 20 of the second characteristic substance shown in FIG. 3, when the absorbances are reversed, a largest value 22 or a maximum value is a positive value, but a smallest value 26 or a minimum value is a negative value. Furthermore, when the absorbances are not reversed, as an exception, in the second narrowband light, a wavelength to be selected is not a wavelength at which the above difference is the smallest value 26 or the minimum value, but it is desirable to select a peak wavelength (not in the same wavelength range) separated from a wavelength at which the above difference is the largest value 22 or the maximum value.

That is, in the present embodiment, one characteristic substance is not specified, but specifying the two characteristic substances 14, 16 is desired. Therefore, when peak wavelengths of the respective characteristic substances are simply selected, it is difficult to specify the characteristic substances, in a case where the peak wavelengths exist at near positions (in the same wavelength range).

Thus, on the basis of the respective absorbances of the first characteristic substance 14 and the second characteristic substance 16, a difference between the absorbances is first calculated at every wavelength. The difference between the absorbances is a value obtained by subtracting an absorbance of the second characteristic substance 16 from that of the first characteristic substance 14. Next, a largest value and a smallest value of the calculated difference between the absorbances are obtained, and narrowband light having a wavelength corresponding to the largest value is selected as the first narrowband light and narrowband light having a wavelength corresponding to the smallest value is selected as the second narrowband light. In this case, if a wavelength range is present in which the absorbance of the second characteristic substance 16 is larger than that of the first characteristic substance 14, the smallest value is negative.

For example, in cases of the optical absorption spectrum 18 of the first characteristic substance and the optical absorption spectrum 20 of the second characteristic substance as shown in FIG. 4, narrowband light having the wavelength that takes the largest value 22 of the difference between the absorbances is selected as first narrowband light 24, and narrowband light having the wavelength that takes the smallest value 26 (the negative value) of the difference between the absorbances is selected as second narrowband light 28.

It is to be noted that instead of the largest value and the smallest value, the maximum value and the minimum value may be employed.

As understood from the above, each of the two characteristic substances 14 and 16 can be specified by selecting the wavelength in which the difference between the absorbances is largest or maximum, or smallest or minimum.

However, when a peak or a bottom of each absorbance of the characteristic substances is noticeable, it is easier to specify the characteristic substance by using the peak or the bottom. Accordingly, in fact, even in a case where the difference between the absorbances is not largest nor maximum or smallest nor minimum, if the difference between the absorbances is large at the peak wavelength and in the vicinity of the peak wavelength of the absorbance of the first characteristic substance 14 (the second characteristic substance 16), this wavelength may be preferentially selected. In this case, the difference between the absorbances is suitably half or more of the largest value.

That is, on the basis of the absorbance at every wavelength of each of the first characteristic substance 14 and the second characteristic substance 16, each of the first narrowband light 24 and the second narrowband light 28 can be selected.

In this case, as the first narrowband light 24 and the second narrowband light 28, narrowband light contained in a third wavelength range containing a wavelength at which an absorbance at every wavelength of each of the first characteristic substance 14 and the second characteristic substance 16 is a largest value or a maximum value, and narrowband light contained in a fourth wavelength range containing a wavelength at which an absorbance at every wavelength of each of the characteristic substances is a smallest value or a minimum value are selected.

Furthermore, in the selection of the first narrowband light 24 and the second narrowband light 28, it is possible to use a ratio of absorbances instead of the difference between an absorbance at every wavelength of the first characteristic substance 14 and an absorbance at every wavelength of the second characteristic substance 16. That is, in the first characteristic substance 14 and the second characteristic substance 16, narrowband light having a wavelength at which an absorbance of one characteristic substance is ½ or less, suitably ⅕ or less and further suitably ⅒ or less of that of the other characteristic substance, and narrowband light having a wavelength at which an absorbance of the other characteristic substance is ½ or less, suitably ⅕ or less and further suitably ⅒ or less of that of the one characteristic substance, as the first narrowband light and the second narrowband light may be selected as the first narrowband light 24 and the second narrowband light 28, respectively.

For example, in cases of the optical absorption spectrum 18 of the first characteristic substance and the optical absorption spectrum 20 of the second characteristic substance as shown in FIG. 5, as the first narrowband light 24, narrowband light having a wavelength at which an absorbance A of the first characteristic substance 14 and an absorbance B of the second characteristic substance 16 have a relation of B/A≤½, suitably B/A≤⅕ and further suitably B/A≤⅒ is selected. As to the second narrowband light 28, although not shown in FIG. 5, the narrowband light having a wavelength at which A/B≤½, suitably A/B≤⅕ and further suitably A/B≤⅒ is selected.

Thus, the light having the wavelength at which the absorbance is extremely different (the absorbance of the one characteristic substance is ½ or less of that of the other characteristic substance) is selected, so that the two characteristic substances 14, 16 can be specified, but when the absorbance is ⅒ or less, the characteristic substances can be separated with further higher precision.

Additionally, the largest value and the smallest value are described with reference to FIG. 4, and A/B≤½ and B/A≤½ are described with reference to FIG. 5, but in other words, it can be considered that the absorbances of the first characteristic substance 14 and the second characteristic substance 16 are reversed. Therefore, in the selection of the first narrowband light 24 and the second narrowband light 28, the narrowband light may be selected from each of ranges where the absorbances of the first characteristic substance 14 and the second characteristic substance 16 are reversed. That is, in the first characteristic substance 14 and the second characteristic substance 16, two kinds of narrowband light having wavelengths at which absorbances are mutually reversed are selected as the first narrowband light 24 and the second narrowband light 28.

Figure 6:
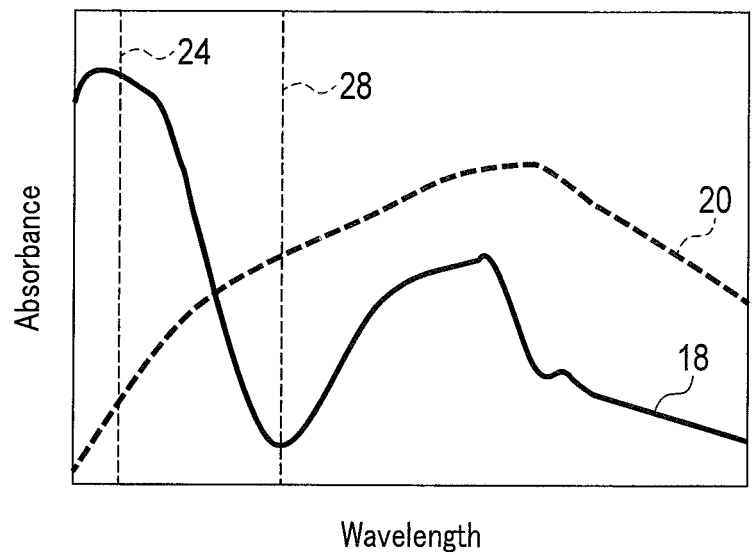
FIG. 6 is a view showing absorption spectra of the first characteristic substance and the second characteristic substance to explain still another example of the selection method of the first narrowband light and the second narrowband light.

For example, in cases of the optical absorption spectrum 18 of the first characteristic substance and the optical absorption spectrum 20 of the second characteristic substance as shown in FIG. 6, the first narrowband light 24 is selected in a wavelength range where the absorbance of the optical absorption spectrum 18 of the first characteristic substance is high and the absorbance of the optical absorption spectrum 20 of the second characteristic substance is low, and the second narrowband light 28 is selected in a wavelength range where the absorbance of the optical absorption spectrum 18 of the first characteristic substance is low and the absorbance of the optical absorption spectrum 20 of the second characteristic substance is high.

Thus, the two kinds of light having the wavelengths at which the absorbances are reversed are selected, so that the two characteristic substances can be specified.

The above-mentioned selection of the first and second narrowband light 24, 28 can automatically be determined in accordance with the selection of the first and second characteristic substances 14, 16. However, it is also possible to present choices of the first and second narrowband light 24, 28 on the basis of the absorbance at every wavelength of each of the first characteristic substance 14 and the second characteristic substance 16 so that the observer selects the intended first narrowband light 24 and second narrowband light 28.

For example, the optical absorption spectrum 18 of the first characteristic substance and the optical absorption spectrum 20 of the second characteristic substance are presented to the observer in accordance with the selection of the first characteristic substance 14 and the second characteristic substance 16. Then, intended wavelengths may be designated as the first narrowband light 24 and the second narrowband light 28 on the basis of the two absorption spectra. In addition to the optical absorption spectrum 18 of the first characteristic substance and the optical absorption spectrum 20 of the second characteristic substance, the choices of the first and second narrowband light 24 and 28 may be presented by using previously stored information on a type of light source mounted in the endoscope. Specifically, the type of light source mounted in the endoscope and including the wavelength range where the ratio of or the difference between the optical absorption spectrum 18 of the first characteristic substance and the optical absorption spectrum 20 of the second characteristic substance is a predetermined value or more may automatically be selected or may be presented to and selected by the observer.

As described above, the first narrowband light 24 and the second narrowband light 28 are selected.

Consequently, as compared with a conventional method of detecting a characteristic substance closely related to a tumor by use of narrowband light in an intended observation region to find a noticeable region (a lesion or the like), it is considered that a method of simultaneously detecting two kinds of characteristic substances closely related to the tumor by use of two kinds of narrowband light further contributes to the improvement of the discovery precision of the noticeable region 12 (the lesion or the like) of the subject 10 that is the intended observation object.

Here, an example where two kinds of characteristic substances and two kinds of narrowband light 24 and 28 are selected is specifically described.

(1) Example where hemoglobin is selected as the first characteristic substance 14 and ICG is selected as the second characteristic substance 16

The hemoglobin is a blood component, and hence detection thereof is effective in predicting a position of a blood vessel closely related to the tumor. Furthermore, ICG is effective in identifying a lung cancer by use of a fluorescence method and by utilization of a phenomenon of congestion in a noncancerous liver tissue excluded from a hepatocellular carcinoma tissue or tumor.

The two kinds of narrowband light 24 and 28 with which such two characteristic substances can be detected are selected in the following manner.

Figure 7:
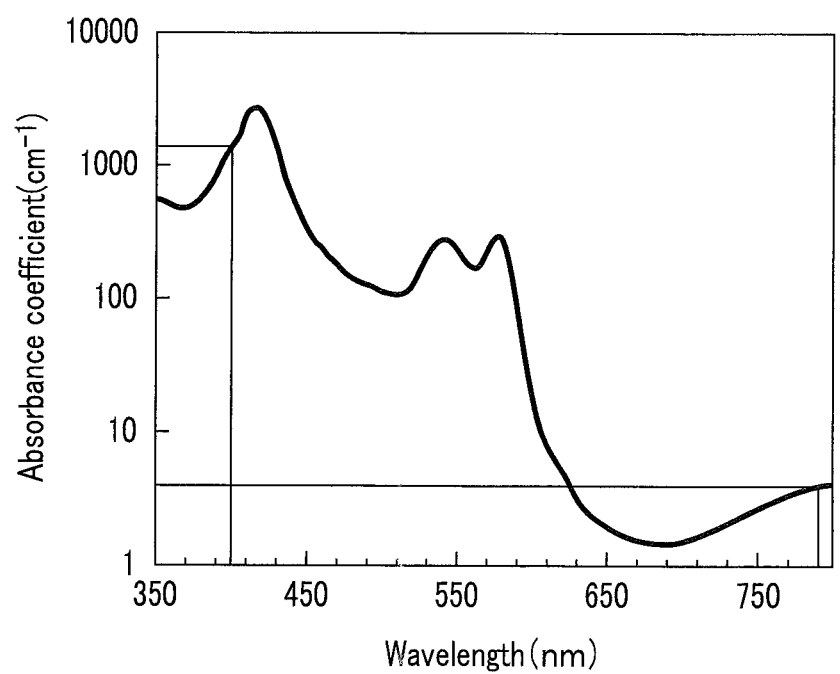
FIG. 7 is a view showing an absorption spectrum of hemoglobin as an example of the first characteristic substance.

Hemoglobin, which is the first characteristic substance 14, has a peak of absorbance in the vicinity of a range of 400 nm to 420 nm and its absorbance is in excess of 1000 at 400 nm as shown in FIG. 7. On the other hand, the absorbance of ICG, which is the second characteristic substance 16, is sufficiently small in the vicinity of 400 nm as shown in FIG. 8. Therefore, a difference between the absorbances in this case is a maximum value, and narrowband light having a wavelength in the vicinity of 400 nm is selected as the first narrowband light 24.

Furthermore, as shown in FIG. 8, ICG, which is the second characteristic substance 16, has a peak (approximately 750) of the absorbance in the vicinity of 790 nm. On the other hand, as shown in FIG. 7, the absorbance of hemoglobin, which is the first characteristic substance 14, is sufficiently small and nearly at its bottom in 790 nm. Consequently, a difference between the absorbances in this case is a smallest value, and narrowband light having a wavelength in the vicinity of 790 nm is selected as the second narrowband light 28.

(2) Example where indigo carmine is selected as the first characteristic substance 14 and ICG is selected as the second characteristic substance 16

Indigo carmine is used in a contrast method of applying a phenomenon where a dye solution accumulates into a dented surface to emphasize surface unevenness in dye endoscope inspection, and is useful for recognition of a lesion. As shown in FIG. 9, indigo carmine has a peak of absorbance at approximately 30 in the vicinity of 610 nm. On the other hand, as shown in FIG. 8, the absorbance of ICG, which is the second characteristic substance 16, is from approximately 0 to 5 in the vicinity of 610 nm. Therefore, a difference between the absorbances in this case is a maximum value, and narrowband light having a wavelength in the vicinity of 610 nm is selected as the first narrowband light 24.

Furthermore, as shown in FIG. 8, ICG, which is the second characteristic substance 16, has a peak (approximately 750) of absorbance in the vicinity of 790 nm. On the other hand, the absorbance of indigo carmine, which is the first characteristic substance 14, is sufficiently small and nearly at its bottom in the vicinity of 790 nm. Therefore, a difference between the absorbances in this case is a minimum value, and narrowband light having a wavelength in the vicinity of 790 nm is selected as the second narrowband light 28.

As described above, as to the method of finding the noticeable region 12 (the lesion or the like) in an intended observation region, two examples have specifically been described where two kinds of characteristic substances and two kinds of narrowband light 24 and 28 are selected. In each of the examples, the two characteristic substances can simultaneously be detected, and hence the example is useful for the improvement of the discovery precision of the noticeable region 12 (the tumor or the like).

The irradiation sequence selecting step of Step S13 is a step to select an irradiation sequence in irradiating the selected first and second narrowband light 24 and 28 in Step S2.

The selectable irradiation sequence includes three irradiation sequences. A first irradiation sequence is a sequence that simultaneously irradiates the first narrowband light 24 and the second narrowband light 28. A second irradiation sequence is a sequence that alternately irradiates the first narrowband light 24 and the second narrowband light 28 switching them every imaging frame of an imager of an imaging section or in one imaging frame. A third irradiation sequence is a sequence that independently irradiates the first narrowband light 24 and the second narrowband light 28.

Therefore, description will hereinafter be made as to a case where the first or second irradiation sequence is selected.

The irradiation sequence is selected from a list by the observer. Here, when the wavelength of the first narrowband light 24 is close to that of the second narrowband light 28, it is suitable that a countermeasure of disposing a filter on an imager side or the like is taken so that the wavelengths of the first narrowband light 24 and the second narrowband light 28 are separable. In the other cases, either one of the irradiation sequences can be selected.

It is to be noted that one of the irradiation sequences, e.g., the second irradiation sequence is only carried out, and needless to say, the irradiation sequence selecting step of Step S13 may be omitted.

Furthermore, in this irradiation sequence selecting step of Step S13, a first irradiation mode that stabilizes the irradiation sequence of the first narrowband light 24 and the second narrowband light 28 and a second irradiation mode that can arbitrarily change the irradiation sequence of the first narrowband light 24 and the second narrowband light 28 may be selectable. Here, in the first irradiation mode, a ratio of irradiation time between the first narrowband light 24 and the second narrowband light 28 is stabilized. Additionally, in the second irradiation mode, the ratio of the irradiation time between the first narrowband light 24 and the second narrowband light 28 can be arbitrarily changed by the observer. For example, the ratio of the irradiation time between the first narrowband light 24 and the second narrowband light 28 may be changed within the following two limitations. A first limitation is that the irradiation time of each of the first narrowband light 24 and the second narrowband light 28 is not less than an irradiation time to acquire each necessary quantity of light when acquiring an image by the first narrowband light 24 and the second narrowband light 28 in the above imaging step of Step S3. A second limitation is that the irradiation time of each of the first narrowband light 24 and the second narrowband light 28 is less than an irradiation time to obtain the image data at a luminance level at which either one of the first luminance image and the second luminance image is not overexposed, when the first luminance image and the second luminance image are formed in an after-mentioned step S41. The quantity of light increases in proportion to the irradiation time. Consequently, the larger the quantity of the light is, the brighter the luminance image to be formed becomes. However, when the quantity of the light excessively increases, the luminance image is overexposed. Therefore, in the second irradiation mode, the luminance image to which importance is attached can be brighter than the other luminance image, depending on a degree of the importance to be attached to each of the first characteristic substance 14 and the second characteristic substance 16 by the observer.

Consequently, when the first and second narrowband light 24 and 28 and the irradiation sequence (and the irradiation mode) are selected, the insertion section of the endoscope is inserted into the body cavity of the subject 10, the first narrowband light 24 and the second narrowband light 28 are irradiated in accordance with the selection in the above narrowband light irradiating step of Step S2.

Then, in the above imaging step of Step S3, the imaging is performed by the imaging section disposed at the distal end of the insertion section of the endoscope. It is assumed that the imager of the imaging section is an imaging element having a color filter of Bayer array.

The above characteristic substance presence image forming step of Step S4 includes a luminance image forming step (Step S41) to form the first luminance image as image information showing presence of the first characteristic substance 14 and the second luminance image as image information showing presence of the second characteristic substance 16, on the basis of the luminance obtained from imaging data.

That is, in the irradiation sequence selecting step of Step S13, when the second irradiation sequence to irradiate alternately is selected, the first narrowband light 24 and the second narrowband light 28 are alternately irradiated in Step S2. Each of the irradiated narrowband light 24 and 28 is reflected by the subject 10 (the noticeable region 12) and received by the Bayer imager of the imaging section. In Step S3, the Bayer imager photoelectrically converts the respective received narrowband light 24 and 28 to accumulate signal charges. Then, in Step S41, an image processor provided in the video processor of an endoscope apparatus reads the signal charge accumulated by the Bayer imager as an imaging signal, to form a first luminance image 30 that is the luminance image regarding the first characteristic substance 14 by use of the first narrowband light 24 and a second luminance image 32 that is the luminance image regarding the second characteristic substance 16 by use of the second narrowband light 28.

It is to be noted that in the irradiation sequence selecting step of Step S13, when the first irradiation sequence, which simultaneously irradiates the first narrowband light 24 and the second narrowband light 28, is selected, the read imaging signals are separated by color, and the first luminance image 30 and the second luminance image 32 can be formed from either one of the separated imaging signals.

Figure 10:
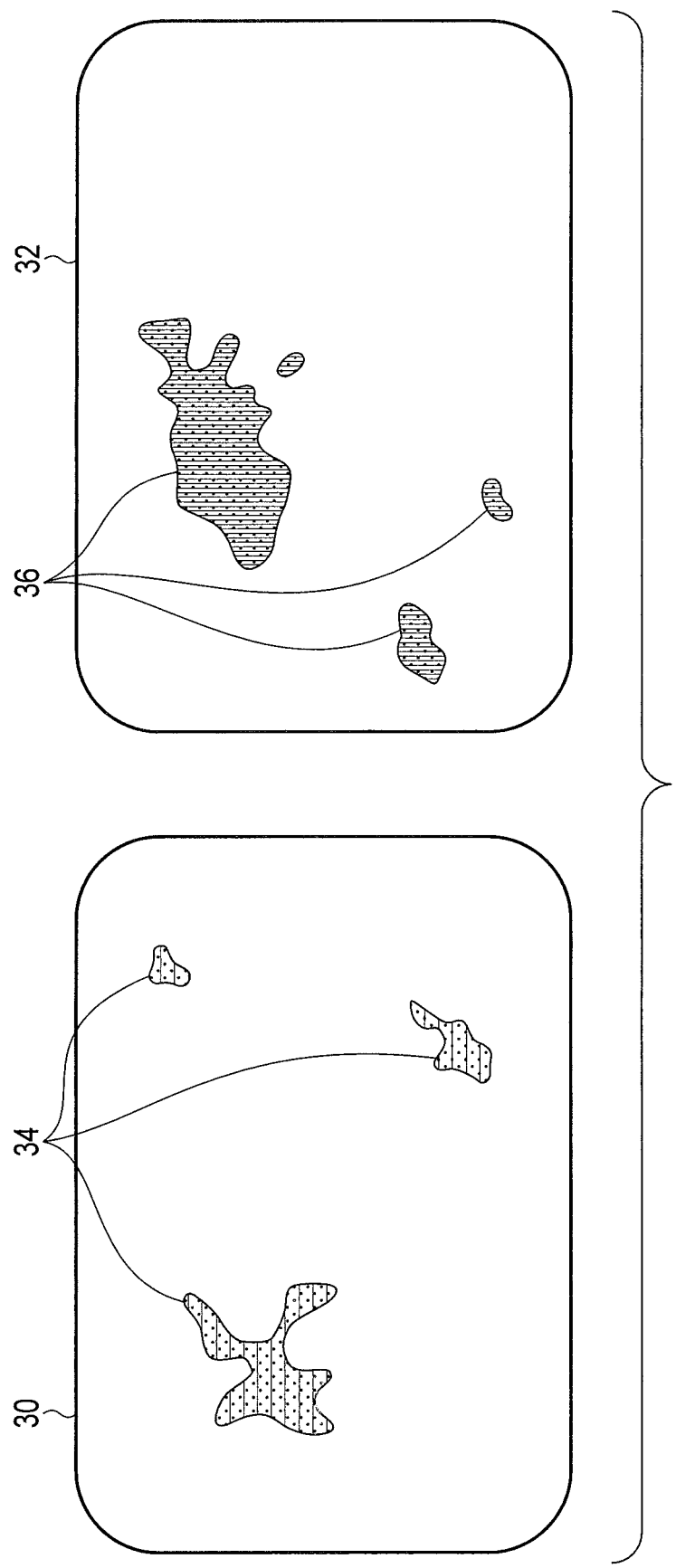
FIG. 10 is a view showing a first luminance image and a second luminance image.

The above characteristic substance presence image forming step of Step S4 further includes a characteristic substance presence judging step (Step S42) to judge the presence or absence of the characteristic substance from contrasts in the luminance images of the formed first luminance image 30 and second luminance image 32. That is, when the noticeable region 12, e.g., the lesion containing the first characteristic substance 14 is present in the subject 10, the first narrowband light 24 is absorbed by the first characteristic substance 14, and a quantity of the reflected light to be received by the Bayer imager decreases. Therefore, as shown in FIG. 10, in the first luminance image 30, regions where the first characteristic substance 14 is present have a low luminance and show up as first characteristic substance images 34. Similarly, when the noticeable region 12, e.g., the lesion containing the second characteristic substance 16 is present in the subject 10, the second narrowband light 28 is absorbed by the second characteristic substance 16, and the quantity of the reflected light to be received by the Bayer imager decreases. Therefore, as shown in FIG. 10, in the second luminance image 32, regions where the second characteristic substance 16 is present have a low luminance and show up as second characteristic substance images 36. Consequently, in the present characteristic substance presence judging step of Step S42, the presence of the first characteristic substance 14 is confirmed from the contrast of the first luminance image 30 that is the luminance image regarding the first characteristic substance 14, and the presence of the second characteristic substance 16 is confirmed from the contrast of the second luminance image 32 that is the luminance image regarding the second characteristic substance 16.

In this case, it may be modified so that the observer can select a value of the contrast steplessly or stepwise according to preference, or the observer can select from previously prepared values for separate use applications.

In consequence, it is possible to easily judge the presence or absence of the characteristic substance from the contrast in the luminance image.

Then, in the above display step of Step S5, the following display is carried out in accordance with results of the judgment in this characteristic substance presence judging step of Step S42.

Figure 11:
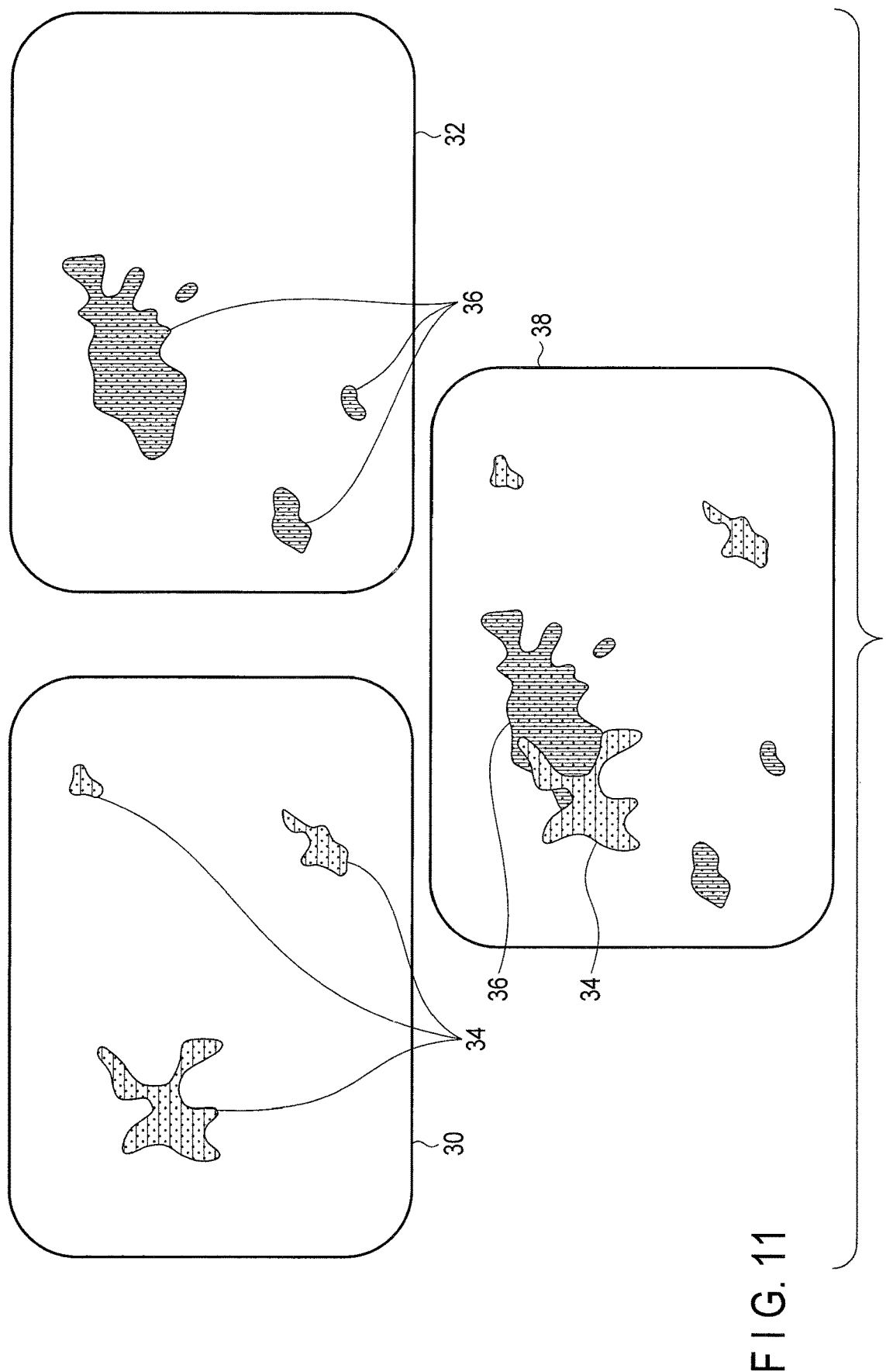
FIG. 11 is a view to explain the formation of a synthetic luminance image of the first luminance image and the second luminance image.

That is, in the characteristic substance presence judging step of Step S42, when the presence of both of the first characteristic substance 14 and the second characteristic substance 16 can be confirmed, as shown in FIG. 11, the first luminance image 30 regarding the first characteristic substance 14 and the second luminance image 32 regarding the second characteristic substance 16 are synthesized, so that a synthesized luminance image 38 is formed and displayed in a display section (Step S51).

Figure 12:
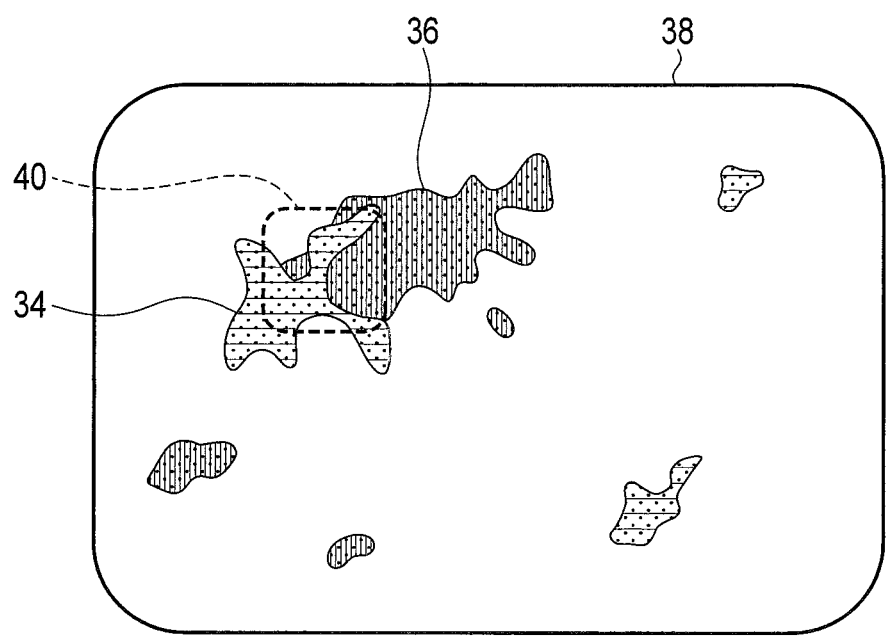
FIG. 12 is a view to explain an overlapping region of the first characteristic substance and the second characteristic substance.

Afterward, an overlapping region only of two characteristic substances of the first characteristic substance 14 and the second characteristic substance 16 is extracted from the synthesized luminance image 38 formed as described above, and the extracted overlapping region of the characteristic substances is distinguishably displayed on the synthesized luminance image 38 so that the overlapping region can be easily distinguished from other regions on the image (Step S52). For example, as shown in FIG. 12, an overlapping presence region 40 including the extracted overlapping region is distinguishably displayed as a rectangular area surrounded with a broken line in red or the like.

Then, the first luminance image 30, the second luminance image 32, and the synthesized luminance image 38 synthesized from the first luminance image and the second luminance image are stored as the image data (Step S53).

Afterward, when the observation is still continued (Step S6), the process returns to the above narrowband light irradiating step of Step S2 to continue the observation. That is, when the same region, the vicinity thereof, another region or the like is to be continuously observed after the image data is stored, the process returns to the narrowband light irradiating step of Step S2.

Figure 13A:
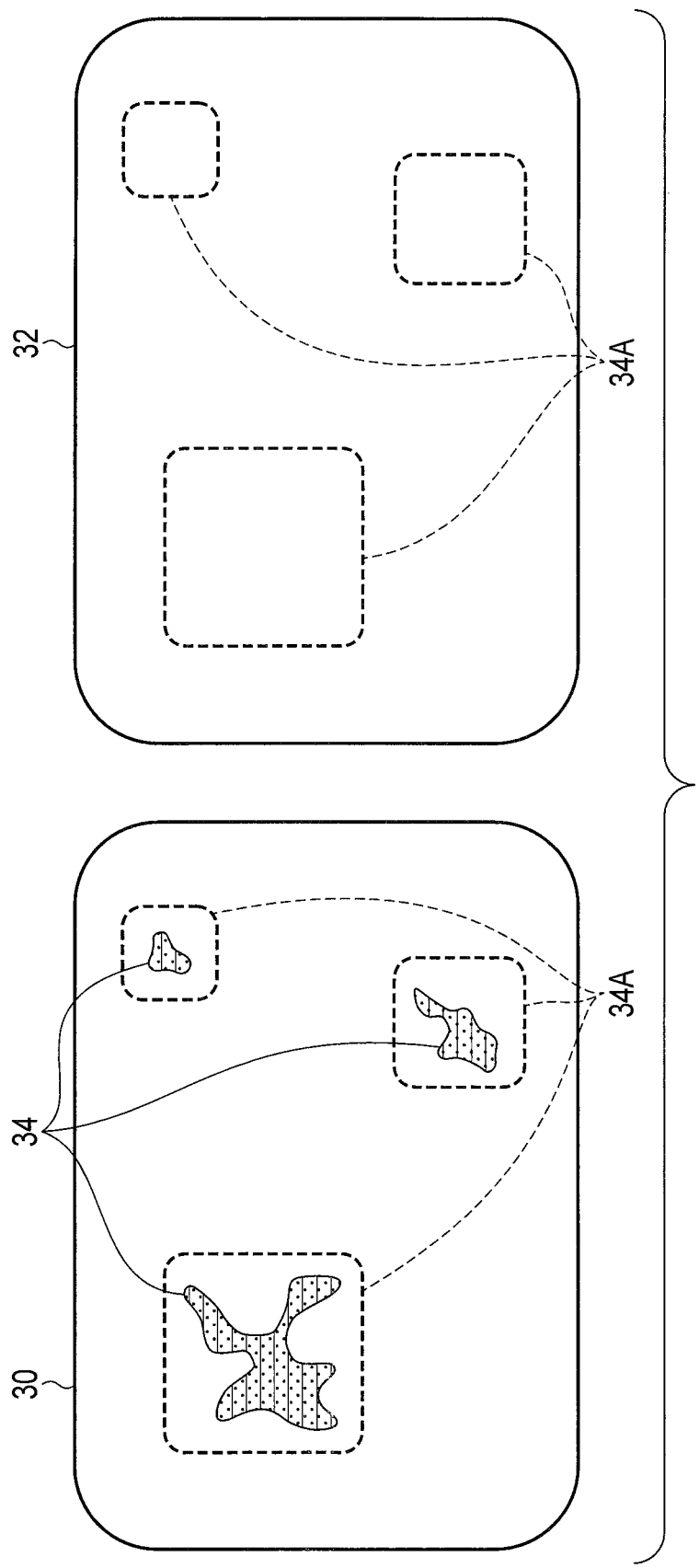
FIG. 13A is a view showing the first luminance image and the second luminance image in a case where the first characteristic substance is only detected.
Figure 13B:
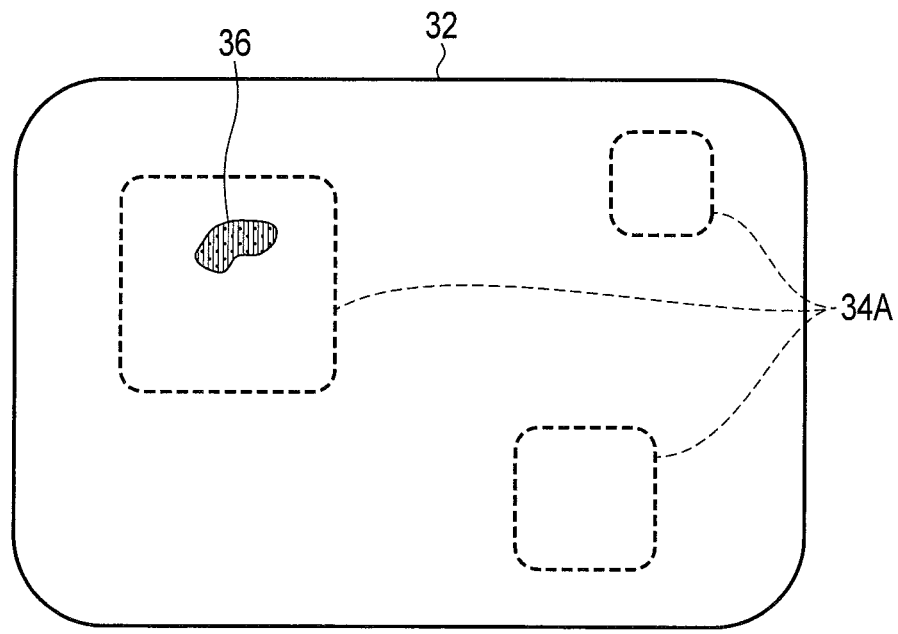
FIG. 13B is a view showing the second luminance image after contrast increase processing that is obtained by increasing contrast for a region of the second luminance image corresponding to a region where the first characteristic substance is detected in the first luminance image of FIG. 13A.

On the other hand, in the characteristic substance presence judging step of Step S42, when the presence of one of the first characteristic substance 14 and the second characteristic substance 16 cannot be confirmed, the contrast of the luminance image regarding the characteristic substance that cannot be confirmed is increased (Step S54). That is, in the characteristic substance presence judging step of Step S42, when it is judged that the contrast value of either one of the first luminance image 30 and the second luminance image 32 is less than the predetermined contrast value, a presence region of the characteristic substance in one luminance image having a contrast value higher than the predetermined contrast value is grasped, and a contrast in the same presence region in the other luminance image is increased. For example, as shown in FIG. 13A, when the first characteristic substance images 34 can be confirmed in the first luminance image 30 regarding the first characteristic substance 14 but when the second characteristic substance images 36 cannot be confirmed in the second luminance image 32 regarding the second characteristic substance 16, presence regions 34A of the first characteristic substance images 34 on the first luminance image 30 are grasped as shown by rectangles surrounded with broken lines in FIG. 13A. Then, on the second luminance image 32 regarding the second characteristic substance 16, the contrast of the same regions as the presence regions 34A is increased, and the second characteristic substance images 36 are extracted. When the contrast is increased so that the contrast of the second characteristic substance images 36 on the second luminance image 32 is the predetermined contrast value or more, the second characteristic substance image shows up on the second luminance image 32 as shown in FIG. 13B.

It is to be noted that the contrast is increased by a contrast increasing method in usual image processing. Specifically, the luminance usually linearly changes, and the contrast can be increased by changing inclination of this straight line to a steeper inclination. In this case, a value that is a certain value or less is set to a smallest luminance, a value that is the certain value or more is set to a largest luminance, and the inclination of a straight line between the values is steepened.

Then, similarly to the above step S52, the first luminance image 30 regarding the first characteristic substance 14 and the second luminance image 32 regarding the second characteristic substance 16 are synthesized to form the synthesized luminance image 38, and the image is displayed in the display section (Step S55). Here, when the second characteristic substance image 36 can be extracted in the above contrast increasing step of Step S54, the synthesized luminance image 38 includes the first characteristic substance image 34 and the second characteristic substance image 36. On the other hand, when the second characteristic substance image 36 cannot be extracted in the above contrast increasing step of Step S54, the synthesized luminance image 38 only includes the first characteristic substance image 34.

Afterward, similarly to the above step S52, the overlapping region of two characteristic substances of the first characteristic substance 14 and the second characteristic substance 16 is extracted from the thus formed synthesized luminance image 38, and the extracted overlapping region of the characteristic substances is distinguishably displayed on the synthesized luminance image 38 so that the overlapping region can be easily distinguished from other regions on the image (Step S56).

Then, similarly to the above step S53, the first luminance image 30, the second luminance image 32, and the synthesized luminance image 38 formed by synthesizing the first luminance image and the second luminance image are stored as the image data (Step S57).

Afterward, when the observation is still continued (Step S6), the process returns to the above narrowband light irradiating step of Step S2 to continue the observation.

Furthermore, in the above characteristic substance presence judging step of Step S42, when it is judged that the contrast value of each of the first luminance image 30 and the second luminance image 32 is less than the predetermined contrast value, i.e., when it is judged that both the two characteristic substances are absent, the first luminance image 30 and the second luminance image 32 are displayed (Step S58). That is, an observation image of the subject 10 in which the noticeable region 12 is not present is displayed.

Afterward, when the observation is still continued (Step S6), the process returns to the above narrowband light irradiating step of Step S2 to continue the observation.

Then, to end the observation (Step S6), the insertion section of the endoscope is removed from the body cavity, which is the subject 10, thereby returning to a usual endoscope stopping operation to end the observation.

Figure 14:
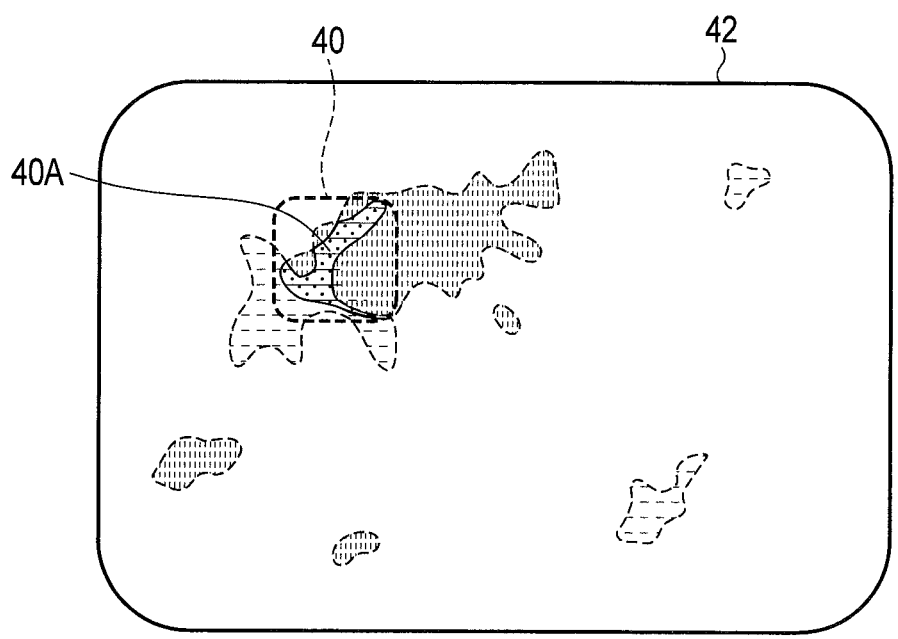
FIG. 14 is a view showing a characteristic substance emphasizing image.

It is to be noted that in the above steps S52 and S56, the overlapping presence region 40 including the extracted overlapping region of the characteristic substances is distinguishably displayed as the rectangular area surrounded with the broken line in red or the like, but a characteristic substance emphasizing image 42 to emphasize and display an actual overlapping region of the characteristic substances may be formed and displayed so that the overlapping region of the characteristic substances can be easily distinguished from other regions on the image. For example, as shown in FIG. 14, the characteristic substance emphasizing image 42 can be an image in which an overlapping region 40A of the characteristic substances is thickly displayed and the other regions are thinly displayed. Additionally, in this case, the distinguishable display of a rectangular area showing the overlapping presence region 40 may be omitted.

There has been described the example where two kinds of characteristic substances are detected with two different kinds of narrowband light 24 and 28, but three kinds of characteristic substances and three kinds of narrowband light may be selected. In this case, the characteristic substances and narrowband light are selected in a combination in which each characteristic substance has a high absorbance for each of the three kinds of narrowband light, and two characteristic substances other than the characteristic substance having the high absorbance have a sufficiently decreased absorbance.

For example, when hemoglobin is selected as the first characteristic substance 14, ICG is selected as the second characteristic substance 16, and indigo carmine is selected as a third characteristic substance as described above, the narrowband light are selected in the following manner.

Firstly, as shown in FIG. 7, hemoglobin, which is the first characteristic substance 14, has a peak of absorbance in the vicinity of a range of 400 nm to 420 nm and its absorbance is in excess of 1000 at 400 nm. On the other hand, absorbances of ICG, which is the second characteristic substance 16, and indigo carmine, which is the third characteristic substance, are sufficiently small in the vicinity of 400 nm as shown in FIG. 8 and FIG. 9. Therefore, a difference between the absorbances in this case is a maximum value, and narrowband light having a wavelength in the vicinity of 400 nm is utilizable as the first narrowband light 24.

Next, as shown in FIG. 8, ICG, which is the second characteristic substance 16, has a peak (approximately 750) of the absorbance in the vicinity of 790 nm, while, as shown in FIG. 7 and FIG. 9, the absorbance of hemoglobin, which is the first characteristic substance 14, and the absorbance of indigo carmine, which is the third characteristic substance, are sufficiently small and nearly at its bottom in the vicinity of 790 nm. Consequently, a difference between the absorbances in this case is a minimum value, and the narrowband light having a wavelength in the vicinity of 790 nm is utilizable as the second narrowband light 28.

Finally, as shown in FIG. 9, indigo carmine, which is the third characteristic substance, has a peak of absorbance that is approximately 30 in the vicinity of 610 nm, while, as shown in FIG. 7 and FIG. 8, the absorbance of hemoglobin, which is the first characteristic substance 14, and the absorbance of ICG, which is the second characteristic substance 16, are sufficiently small in the vicinity of 610 nm. Therefore, a difference between the absorbances in this case is a maximum value, and narrowband light having a wavelength in the vicinity of 610 nm is utilizable as third narrowband light.

It is to be noted that steps of and after the narrowband light irradiating step of Step S2 are similar to those of the example where two kinds of narrowband light and two kinds of characteristic substances are utilized.

Furthermore, the characteristic substances are not limited to the above hemoglobin, ICG, and indigo carmine.

For example, methylene blue indicating optical absorption spectrum as in FIG. 15 can be selected. As shown in the drawing, for light having a wavelength of 670 nm, methylene blue is completely distinguishable from hemoglobin (in the vicinity of 400 nm) and ICG (in the vicinity of 790 nm), and is also distinguishable from indigo carmine (in the vicinity of 610 nm) because there is about double difference between the absorbances. Consequently, a combination of methylene blue and 670 nm can be selected as a combination of a fourth characteristic substance and a fourth wavelength.

As described above, any substance contained in the noticeable region 12, e.g., the lesion is utilizable as the characteristic substance.

Figure 16:
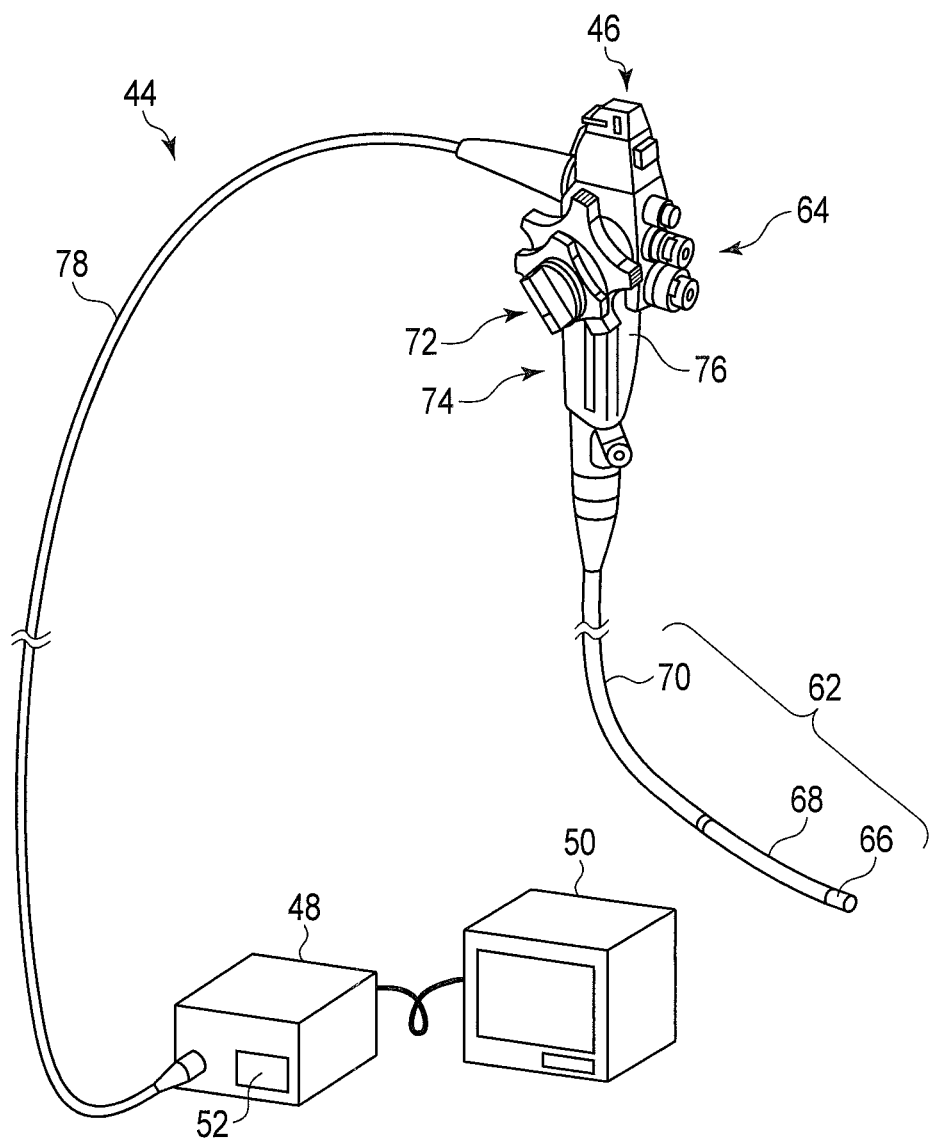
FIG. 16 is an external view of an endoscope apparatus to perform an endoscope observation method according to an embodiment of the present invention.
Figure 17:
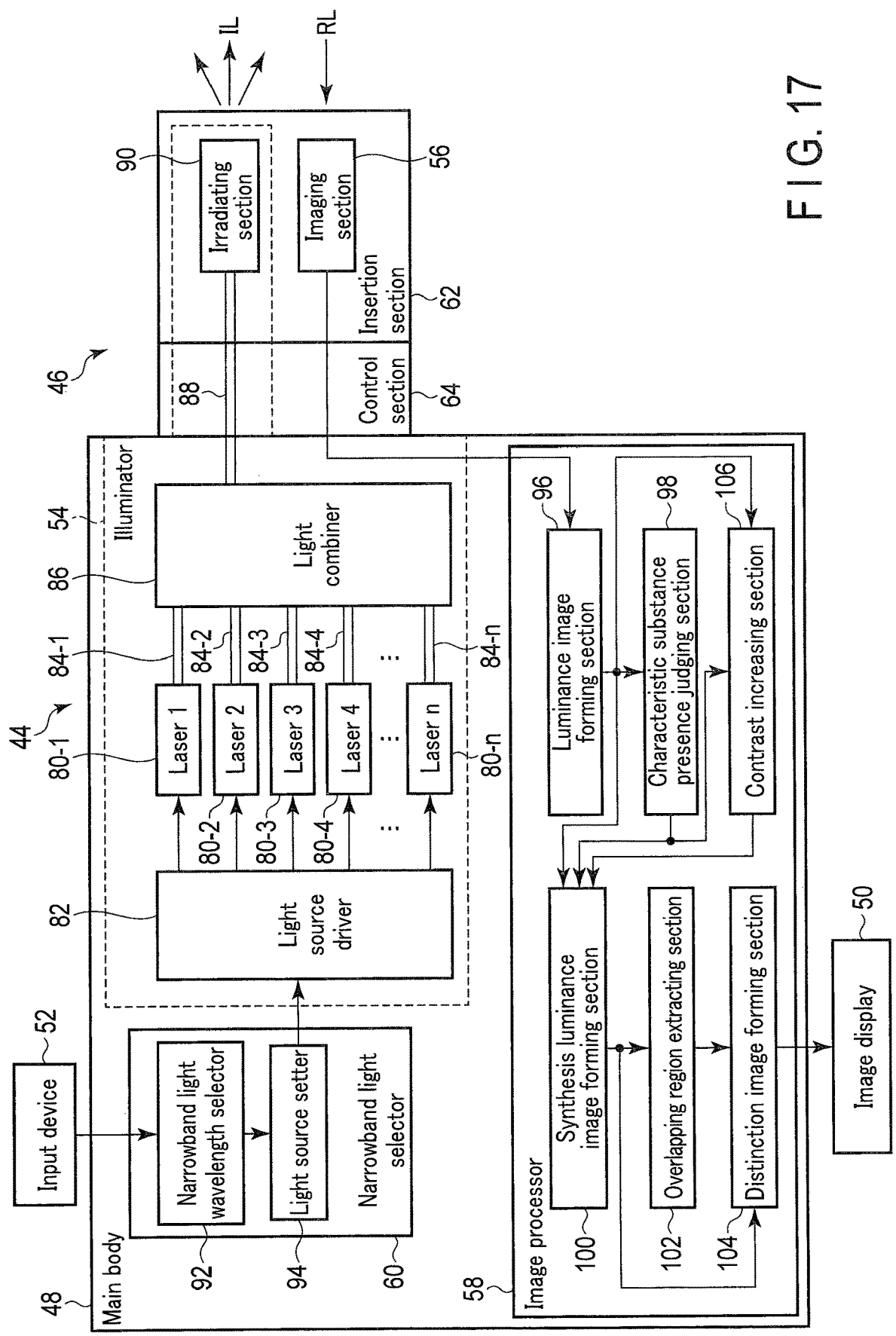
FIG. 17 is a block diagram showing an example of a schematic constitution of the endoscope apparatus.

Here, description is made as to the endoscope apparatus to perform an endoscope observation method according to the present embodiment, with reference to an external view of FIG. 16 and a block diagram of FIG. 17.

An endoscope apparatus 44 has an endoscope 46, a main body (a video processor) 48, an image display (a monitor) 50, and an input device 52. An illuminator 54 is disposed through the endoscope 46 and the main body 48, to irradiate the first and second narrowband light 24 and 28 as illumination light IL to the subject 10 that might contain the noticeable region 12.

The endoscope 46 includes an imaging section 56 that detects reflected light RL of the illumination light IL irradiated to the subject 10 that might contain the noticeable region 12 to output the imaging signal. The input device 52 is connected to the main body 48 or disposed on the main body 48, to input various observer instructions into the main body 48. The main body 48 includes an image processor 58 that forms a display image from the imaging signal of the imaging section 56 of the endoscope 46, and a narrowband light selector 60 that sets the illuminator 54 in accordance with the selection input into the input device 52. The image display 50 is connected to the main body 48, and displays, as an observation object image, the display image formed by the image processor 58.

In the endoscope 46, there are arranged an elongate insertion section 62 that is a bendable member and a control section 64 coupled with a proximal end of the insertion section 62.

The insertion section 62 has a distal end hard section 66, a bendable section 68 that bends, and a flexible tube section 70 from a distal end side of the insertion section 62 toward the proximal end side. Here, a proximal end of the distal end hard section 66 is coupled with a distal end of the bendable section 68 and a proximal end of the bendable section 68 is coupled with a distal end of the flexible tube section 70.

The distal end hard section 66 is at the distal end of the insertion section 62 and a distal end of the endoscope 46, and is constituted by a hard member. In the distal end hard section 66, the imaging section 56 is provided.

The bendable section 68 bends in a desired direction in accordance with an operation of a bend control section 72 disposed in the control section 64 by the observer (an operator such as a surgeon). The observer operates the bend control section 72 to bend the bendable section 68. Thus, the bendable section 68 is bent, thereby changing a position and an orientation of the distal end hard section 66, and the observation region of the subject 10 is captured in an observation field of vision. The illumination light IL from the illuminator 54 is irradiated to the observation region captured in this way, to illuminate the observation region. The bendable section 68 is constituted by coupling unshown joint rings along a longitudinal direction of the insertion section 62.

The flexible tube section 70 has a desired flexibility and is bent by an external force. The flexible tube section 70 is a tubular member extending from a main body section 74 of the control section 64.

The control section 64 has the main body section (a scope) 74, a grip 76, and a universal cord 78. The flexible tube section 70 extends out from a distal end of the main body section 74. The grip 76 is coupled with a proximal end of the main body section 74 and is gripped by the observer who operates the endoscope 46. The universal cord 78 connects between the grip 76 and the main body 48.

In the grip 76, the bend control section 72 is disposed to operate unshown operating wires to bend the bendable section 68. The bend control section 72 has a left and right bend control knob to bend the bent section 68 left and right, an up and down bend control knob to bend the bendable section 68 up and down, and a fixing knob to fix a position of the bent bendable section 68.

The left and right bend control knob is connected to an unshown left and right bend control driver to be driven with the left and right bend control knob. Furthermore, the up and down bend control knob is connected to an unshown up and down bend control driver to be driven with the up and down bend control knob. The up and down bend control driver and the left and right bend control driver are arranged, for example, in the grip 76.

The left and right bend control driver is connected to an unshown left and right operating wire inserted into the control section 64, the flexible tube section 70, and the bendable section 68, and both ends of the left and right operating wire are connected to the distal end of the bendable section 68.

Furthermore, the up and down bend control driver is connected to an unshown up and down operating wire inserted into the control section 64, the flexible tube section 70, and the bendable section 68. The up and down operating wire is separate from the left and right operating wire, and the wires can be mutually independently operated. Both ends of the up and down operating wire are connected to the distal end of the bendable section 68.

The left and right bend control knob is configured to bend the bendable section 68 left and right through the left and right bend control driver and the left and right operating wire. Furthermore, the up and down bend control knob is configured to bend the bendable section 68 up and down through the up and down bend control driver and the up and down operating wire.

Thus, the bend control section 72 (the left and right bend control knob and the up and down bend control knob), the left and right bend control driver, the left and right operating wire, the up and down bend control driver, and the up and down operating wire constitute a bend control mechanism that operates the bendable section 68 to bend the bendable section 68.

Hereinafter, respective components will be described in more detail.

<Input Device 52>

The input device 52 is configured to perform the above-mentioned characteristic substance selecting step of Step S11 and the above-mentioned irradiation sequence selecting step of Step S13.

The observer can perform the selection of the characteristic substance and the selection of the irradiation sequence through the input device 52, and selection information indicating the selected results are output to the narrowband light selector 60 of the main body 48. Furthermore, if necessary, the observer may perform the selection of the narrowband light, the selection of the irradiation mode or selection of the contrast value through the input device 52.

<Illuminator 54>

The illuminator 54 is configured to perform the above-mentioned narrowband light irradiating step of Step S2.

Specifically, the illuminator 54 has plural (n) laser light sources 80-1 to 80-$n$, a light source driver 82, n optical fibers 84-1 to 84-$n$, a light combiner 86, an optical fiber 88, and an irradiating section 90. The laser light sources 80-1 to 80-$n$, the light source driver 82, the optical fibers 84-1 to 84-$n$, the light combiner 86, and a part of the optical fiber 88 are arranged in the main body 48, and the remaining part of the optical fiber 88 and the irradiating section 90 are arranged in the endoscope 46.

Here, the laser light source 80-1 (laser 1) is a laser light source that emits the narrowband light (laser light) having a peak wavelength of, e.g., 400 nm. The laser light source 80-2 (laser 2) is a laser light source that emits the narrowband light (laser light) having a peak wavelength of, e.g., 590 nm. The laser light source 80-3 (laser 3) is a laser light source that emits the narrowband light (laser light) having a peak wavelength of, e.g., 610 nm. The laser light source 80-4 (laser 4) is a laser light source that emits the narrowband light (laser light) having a peak wavelength of, e.g., 780 nm. Each of the laser light source 80-5 (laser 5) to the laser light source 80-$n$ (laser n) is a laser light source that emits another selectable narrowband light (laser light).

The light source driver 82 controls driving of the laser light sources 80-1 to 80-$n$.

The optical fibers 84-1 to 84-$n$ guide, to the light combiner 86, the narrowband light emitted from each of the laser light sources 80-1 to 80-$n$.

The light combiner 86 is, for example, an optical fiber combiner that combines the narrowband light emitted from the laser light sources 80-1 to 80-$n$ and guided through the optical fibers 84-1 to 84-$n$.

The optical fiber 88 guides, to the irradiating section 90, the narrowband light combined by the light combiner 86.

The irradiating section 90 is disposed in the distal end hard section 66 of the insertion section 62 in which the imaging section 56 is disposed. The irradiating section 90 converts optical characteristics of the narrowband light guided from the main body 48 through the optical fiber 88 inserted into the universal cord 78, the control section 64, and the insertion section 62 of the endoscope 46, to irradiate the illumination light IL to the subject 10. The irradiating section 90 has, for example, a function of diffusing the narrowband light guided through the optical fiber 88 and converting light distribution to desired light distribution. The irradiating section 90 does not convert the wavelength of the light.

<Imager 56>

The imaging section 56 is configured to perform the above-mentioned imaging step of Step S3.

The imaging section 56 detects the reflected and scattered light RL from the subject 10 to generate the imaging signal. The imaging signal is output to the image processor 58 of the main body 48.

The imaging section 56 includes Bayer imager having three kinds of light detection elements of an R light detection element that detects a red range, a G light detection element that detects a green range, and a B light detection element that detects a blue range, by use of a color filter. Specifically, the Bayer imager comprises a CCD imager or a CMOS imager.

<Narrowband Light Selector 60>

The narrowband light selector 60 is configured to perform the above-mentioned narrowband light wavelength selecting step of Step S12 and the above-mentioned irradiation sequence selecting step of Step S13.

The narrowband light selector 60 has a narrowband light wavelength selector 92 and a light source setter 94.

The narrowband light wavelength selector 92 selects the first narrowband light 24 and the second narrowband light 28 so that the difference between and/or the ratio of an absorbance at every wavelength of the first characteristic substance 14 and an absorbance at every wavelength of the second characteristic substance 16 selected through the input device 52 is the predetermined value or more.

Specifically, the narrowband light wavelength selector 92 selects, as the first narrowband light 24 and the second narrowband light 28, narrowband light contained in a first wavelength range containing a wavelength at which a difference between an absorbance at every wavelength of the first characteristic substance 14 and an absorbance at every wavelength of the second characteristic substance 16 is a largest value or a maximum value, and narrowband light contained in a second wavelength range containing a wavelength at which the above difference is a smallest value or a minimum value.

Alternatively, the narrowband light wavelength selector 92 selects, in the first characteristic substance 14 and the second characteristic substance 16, narrowband light having a wavelength at which an absorbance of one characteristic substance is ½ or less, suitably ⅕ or less, and further suitably ¹⁄₁₀ or less of that of the other characteristic substance, and narrowband light having a wavelength at which an absorbance of the other characteristic substance is ½ or less, suitably ⅕ or less, and further suitably ¹⁄₁₀ or less of that of the one characteristic substance, as the first narrowband light 24 and the second narrowband light 28, respectively.

Alternatively, the narrowband light wavelength selector 92 selects, as the first narrowband light 24 and the second narrowband light 28, two kinds of narrowband light having wavelengths at which the absorbances of the first characteristic substance 14 and the second characteristic substance 16 are mutually reversed.

The light source setter 94 outputs, to the light source driver 82 of the illuminator 54, light source output pattern information indicating an emission combination and an emission pattern of the laser light sources 80-1 to 80-$n$ in accordance with the selection information from the narrowband light wavelength selector 92 regarding the first and second narrowband light 24 and 28 and the irradiation sequence selected through the input device 52.

The light source driver 82 controls lighting of the respective laser light sources 80-1 to 80-$n$ in accordance with this light source output pattern information.

The narrowband light selector 60 (one or both of the narrowband light wavelength selector 92 and the light source setter 94) may be constituted of a hardware circuit or a processor. In a case of the constitution of the processor, a program code to be executed by the processor so that the processor functions as the narrowband light selector 60 (the narrowband light wavelength selector 92 and/or the light source setter 94) is previously stored in an unshown processor accessible external memory.

<Image Processor 58>

The image processor 58 is configured to perform the above-mentioned luminance image forming step of Step S41, the two characteristic substance presence judging step of Step S42, the synthesized luminance image formation and display step of Step S51, the overlapping region extraction and display step of Step S52, the absence characteristic substance contrast increasing step of Step S54, the synthesized luminance image formation and display step of Step S55, the overlapping region extraction and display step of Step S56, and the luminance image display step of Step S58. In this connection, needless to say, the image processor may perform the data storing steps of Step S53 and Step S57.

The image processor 58 has a luminance image forming section 96, a characteristic substance presence judging section 98, a synthesis luminance image forming section 100, an overlapping region extracting section 102, a distinction image forming section 104, and a contrast increasing section 106.

The luminance image forming section 96 is configured to perform the above-mentioned luminance image forming step of Step S41. That is, the luminance image forming section 96 forms, as the characteristic substance presence images, the first luminance image 30 of the image information indicating the presence of the first characteristic substance 14 and the second luminance image 32 of the image information indicating the presence of the second characteristic substance 16 on the basis of the luminance obtained from the imaging data. The formed first and second luminance images 30 and 32 are output to the characteristic substance presence judging section 98 and the contrast increasing section 106.

The characteristic substance presence judging section 98 is configured to perform the above-mentioned two characteristic substance presence judging step of Step S42. That is, the characteristic substance presence judging section 98 judges the presence or absence of the characteristic substance from the luminance image contrast in each of the first luminance image 30 and the second luminance image 32 that are formed by the luminance image forming section 96. The judgment result is output to the synthesis luminance image forming section 100 and the contrast increasing section 106.

The synthesis luminance image forming section 100 is configured to perform the above-mentioned synthesized luminance image formation and display steps of Step S51 and Step S55 and the luminance image display step of Step S58. That is, the synthesis luminance image forming section 100 synthesizes two luminance images of the first luminance image 30 and the second luminance image 32 that are formed by the luminance image forming section 96, to form the synthesized luminance image 38, when it is judged that the two characteristic substances are present in the characteristic substance presence judging section 98. The formed synthesized luminance image 38 is output to the overlapping region extracting section 102 and the distinction image forming section 104. Furthermore, when it is judged in the characteristic substance presence judging section 98 that both of two characteristic substances are not present, the synthesis luminance image forming section 100 does not synthesize the first luminance image 30 and the second luminance image 32 that are formed by the luminance image forming section 96, and the images may be output to the image display 50 as they are.

The overlapping region extracting section 102 is configured to perform the above-mentioned overlapping region extraction and display steps of Step S52 and Step S56. That is, the overlapping region extracting section 102 extracts only the overlapping region of the first characteristic substance 14 and the second characteristic substance 16 from the synthesized luminance image 38 formed by the synthesis luminance image forming section 100. Information of the extracted overlapping region is output to the distinction image forming section 104.

The distinction image forming section 104 performs processing to the synthesized luminance image 38 to distinguishably display the overlapping region 40A extracted by the overlapping region extracting section 102 on the synthesized luminance image 38 formed by the synthesis luminance image forming section 100. In this processing, as shown in FIG. 12, the image is processed to distinguishably display the overlapping presence region 40 containing the overlapping region 40A as a rectangular area surrounded with a broken line in red or the like. Alternatively, as shown in FIG. 14, the section processes the synthesized luminance image 38 to thickly display the overlapping region 40A and to thinly display the other regions.

The contrast increasing section 106 is configured to perform the above-mentioned absence characteristic substance contrast increasing step of Step S54. That is, when it is judged in the characteristic substance presence judging section 98 that the contrast value of either one of the first luminance image 30 and the second luminance image 32 is less than the predetermined contrast value, the contrast increasing section 106 grasps the presence region of the characteristic substance in the one luminance image having a contrast value higher than the predetermined contrast value in the first luminance image 30 and the second luminance image 32 that are formed by the luminance image forming section 96, and the contrast increasing section increases the contrast in the same presence region in the other luminance image. The other luminance image having the contrast increased is output to the synthesis luminance image forming section 100. Consequently, the synthesis luminance image forming section 100 synthesizes two luminance images of one luminance image given from the luminance image forming section 96 and the other luminance image having the increased contrast given by the contrast increasing section 106 to form the synthesized luminance image 38.

It is to be noted that the image processor 58 (at least one of the luminance image forming section 96, the characteristic substance presence judging section 98, the synthesis luminance image forming section 100, the overlapping region extracting section 102, the distinction image forming section 104, and the contrast increasing section 106) may be constituted of a hardware circuit or a processor. In a case of the constitution of the processor, a program code to be executed by the processor so that the processor functions as the image processor 58 (at least one of the luminance image forming section 96, the characteristic substance presence judging section 98, the synthesis luminance image forming section 100, the overlapping region extracting section 102, the distinction image forming section 104, and the contrast increasing section 106) is previously stored in the unshown processor accessible external memory.

<Image Display 50>

The image display 50 displays the display image formed by the image processor 58. The image display 50 is a monitor such as a liquid crystal display.

It is to be noted that the constitution of the endoscope apparatus 44 shown in FIG. 17 is an example where an observer's selecting operation is received, to perform the above-mentioned narrowband light selecting step of Step S1, i.e., the above-mentioned characteristic substance selecting step of Step S11, the narrowband light wavelength selecting step of Step S12, and the irradiation sequence selecting step of Step S13.

However, irrespective of the observer's selecting operation, it is possible to limit to a specific kind of the noticeable region 12, and select the number of the characteristic substances corresponding to the kind of the noticeable region 12, e.g., two characteristic substances, thereby constituting the endoscope apparatus 44 for exclusive use. That is, the selection may be performed by a manufacturer side of the endoscope apparatus 44 in place of the observer.

Figure 18:
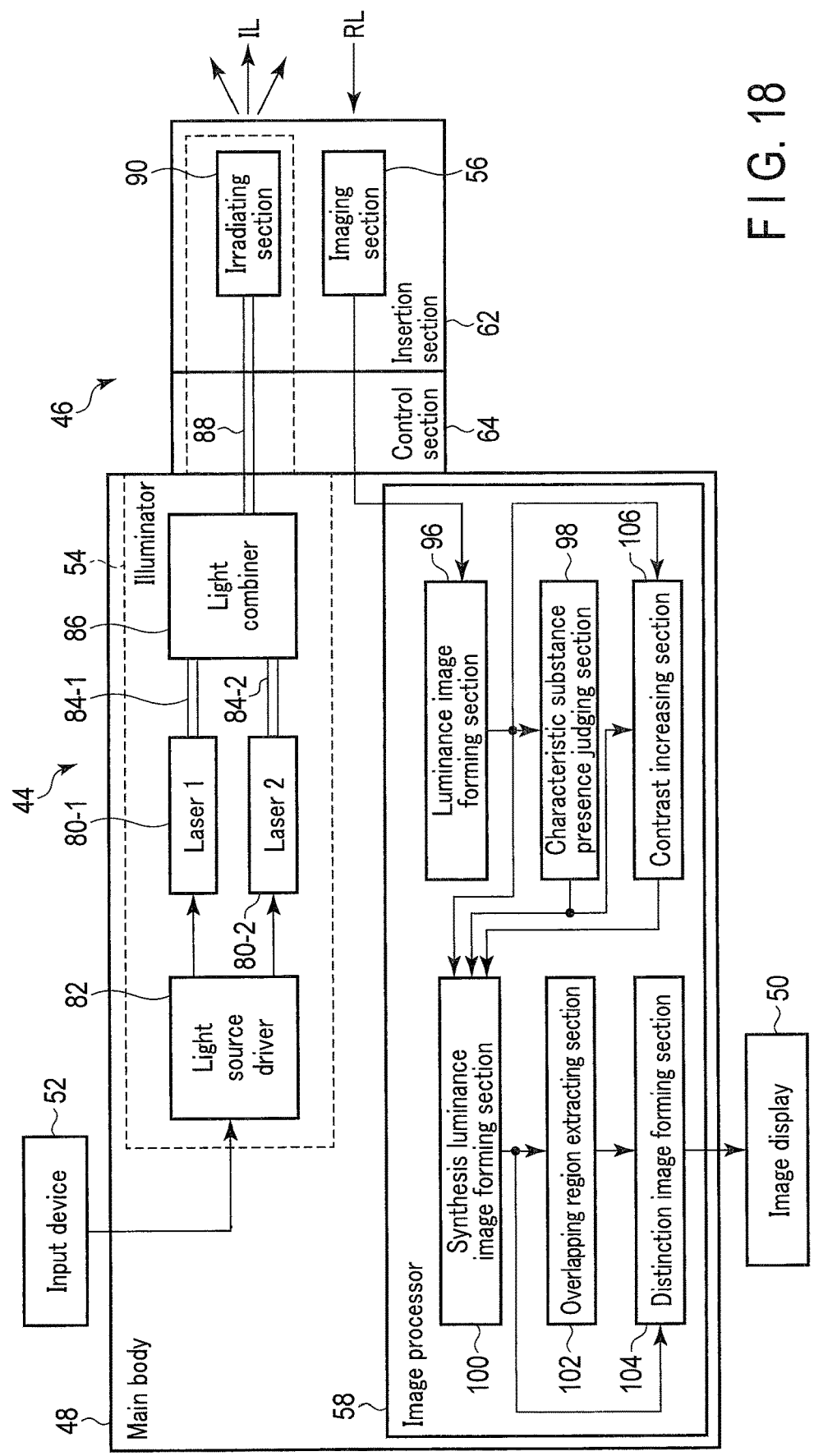
FIG. 18 is a block diagram showing another example of the schematic constitution of the endoscope apparatus.

For example, in the case of the exclusive endoscope apparatus 44 in which two characteristic substances are selected, as shown in FIG. 18, in the illuminator 54, the wavelengths of the first and second narrowband light 24 and 28 are determined on the basis of the previously selected first and second characteristic substances 14 and 16, and hence two laser light sources 80-1 and 80-2 that emit narrowband light (laser light) having the wavelengths may only be mounted. The input device 52 is not used in the selecting operation, but is used in inputting an observation start instruction or the like.

It is to be noted that here, the endoscope apparatus 44 is described in which two characteristic substances are selected and the two laser light sources 80-1 and 80-2 are only mounted, but needless to say, in the exclusive endoscope apparatuses 44, the number of the characteristic substances and the number of the laser light sources is not limited to two.

As described above, the endoscope observation method according to the present embodiment includes the narrowband light selecting step (Step S1) to select the first narrowband light 24 and the second narrowband light 28 having the wavelengths at which absorbances of the first characteristic substance 14 and the second characteristic substance 16 contained in the noticeable region 12 that is the intended observation object are mutually different, the narrowband light irradiating step (Step S2) to irradiate the first narrowband light 24 and the second narrowband light 28 to the observation object, the imaging step (Step S3) to perform the imaging by use of the reflected light of the first narrowband light 24 and the reflected light of the second narrowband light 28 from the observation object, the characteristic substance presence image forming step (Step S4) to form the characteristic substance presence image indicating the presence of the first characteristic substance and the second characteristic substance on the basis of the imaging data obtained in the imaging step, and the display step (Step S5) to display the characteristic substance presence image.

Thus, the first and second narrowband light are irradiated to the subject 10, for the characteristic substances 14, 16 closely related to the noticeable region 12 that is the intended observation object, the first and second narrowband light having the wavelengths at which the absorbances of the respective characteristic substances are mutually different, so that the characteristic substances 14, 16 related to the noticeable region 12 can be detected, and as a result, it is possible to improve the discovery precision of the observation object.

Here, in the narrowband light selecting step (Step S1), the first narrowband light 24 and the second narrowband light 28 can be selected so that the difference between an absorbance at every wavelength of the first characteristic substance 14 and an absorbance at every wavelength of the second characteristic substance 16 is the predetermined value or more.

For example, the narrowband light selecting step (Step S1) includes the narrowband light wavelength selecting step (Step S12) to select the narrowband light contained in the first wavelength range containing the wavelength at which the difference between the absorbance at every wavelength of the first characteristic substance 14 and the absorbance at every wavelength of the second characteristic substance 16 is the largest value or the maximum value and the narrowband light contained in the second wavelength range containing the wavelength at which the above difference is the smallest value or the minimum value, as the first narrowband light 24 and the second narrowband light 28, respectively.

That is, when the narrowband light 24, 28 are selected, one characteristic substance is not specified, but specifying the two characteristic substances 14, 16 is desired. Therefore, when peak wavelengths of the respective characteristic substances are simply selected, it is difficult to specify the characteristic substances in a case where the peak wavelengths are close to each other (in the same wavelength range). To eliminate the problem, the wavelength at which the difference between the absorbances is largest or maximum, or smallest or minimum is selected so that the two characteristic substances 14, 16 can be specified. The selection is not limited to the peak wavelength of each characteristic substance, and there exists a wavelength that is usable if the selection conditions are satisfied.

Alternatively, the narrowband light selecting step (Step S1) can include the narrowband light wavelength selecting step (Step S12) to select, in the first characteristic substance 14 and the second characteristic substance 16, narrowband light having a wavelength at which an absorbance of one characteristic substance is $\frac{1}{2}$ or less, suitably $\frac{1}{5}$ or less, and further suitably $\frac{1}{10}$ or less of that of the other characteristic substance, and narrowband light having a wavelength at which an absorbance of the other characteristic substance is $\frac{1}{2}$ or less, suitably $\frac{1}{5}$ or less, and further suitably $\frac{1}{10}$ or less of that of the one characteristic substance, as the first narrowband light 24 and the second narrowband light 28, respectively.

That is, by the selection of the wavelength at which the absorbances are excessively different (the absorbance is $\frac{1}{2}$ or less, suitably $\frac{1}{5}$ or less, and further suitably $\frac{1}{10}$ or less of that of the one characteristic substance), two characteristic substances can be specified.

Alternatively, the narrowband light selecting step (S1) can include the narrowband light wavelength selecting step (Step S12) to select two kinds of narrowband light having the wavelengths at which the absorbances of the first characteristic substance 14 and the second characteristic substance 16 are mutually reversed, as the first narrowband light 24 and the second narrowband light 28.

That is, by the selection of the wavelength at which the absorbances are reversed, two characteristic substances can be specified.

Furthermore, in the endoscope observation method according to the present embodiment, it is possible to select each of the first narrowband light 24 and the second narrowband light 28 on the basis of the absorbance at every wavelength of each of the first characteristic substance 14 and the second characteristic substance 16.

In this case, the narrowband light selecting step (Step S1) can include the narrowband light wavelength selecting step (Step S12) to select the narrowband light contained in a third wavelength range containing a wavelength at which the absorbance at every wavelength of each of the first characteristic substance 14 and the second characteristic substance 16 is the largest value or the maximum value, and the narrowband light contained in a fourth wavelength range containing a wavelength at which the absorbance at every wavelength of each of the characteristic substances is the smallest value or the minimum value, as the first narrowband light 24 and the second narrowband light 28, respectively.

Additionally, in the endoscope observation method according to the present embodiment, the narrowband light selecting step (Step S1) can further include the characteristic substance selecting step (Step S11) to select the first characteristic substance 14 and the second characteristic substance 16, and the narrowband light wavelength selecting step (Step S12) to select the first narrowband light 24 and the second narrowband light 28 in accordance with these selected first and second characteristic substances 14 and 16.

Furthermore, in the endoscope observation method according to the present embodiment, the narrowband light selecting step (Step S1) further includes the irradiation sequence selecting step (Step S13) to select the irradiation sequence that simultaneously, alternately, or independently irradiates the first narrowband light 24 and the second narrowband light 28.

Here, this irradiation sequence selecting step (Step S13) can include an irradiation mode selecting step to select the first irradiation mode that stabilizes the irradiation sequence of the first narrowband light 24 and the second narrowband light 28, and the second irradiation mode that can arbitrarily change the irradiation sequence of the first narrowband light 24 and the second narrowband light 28.

Thus, the observer can select the irradiation sequence as intended.

Furthermore, in the endoscope observation method according to the present embodiment, the characteristic substance presence image forming step (Step S4) includes the luminance image forming step (Step S41) to form the first luminance image 30 as the image information showing the presence of the first characteristic substance 14 and the second luminance image 32 as the image information showing the presence of the second characteristic substance 16 as the characteristic substance presence image, on the basis of the luminance obtained from the imaging data.

Additionally, the characteristic substance presence image forming step (Step S4) further includes the characteristic substance presence judging step (Step S42) to judge the presence or absence of the characteristic substance from a contrast in each of the first luminance image 30 and the second luminance image 32 formed in the luminance image forming step (Step S41).

In this way, the presence or absence of the characteristic substance can easily be judged from the contrast in the luminance image.

It is to be noted that the characteristic substance presence judging step (Step S42) can include a contrast value setting step to select the value of the contrast arbitrarily or from the previously prepared values for the separate use applications.

Consequently, it is possible to switch among judgment standards for the presence or absence of the characteristic substance in accordance with an observer's way to use, degree of skill or the like.

Additionally, the display step (Step S5) includes the synthesized luminance image display step (Step S51) to synthesize two luminance images of the first luminance image 30 and the second luminance image 32 to form and display the synthesized luminance image 38.

In consequence, the position of each characteristic substance can be confirmed on one observation image, and hence it is easy for the observer to judge whether the region is the noticeable region 12 of the lesion or the like.

Furthermore, in this case, the display step (Step S5) further includes the overlapping region extraction and display step (Step S52) to extract only the overlapping region of the first characteristic substance 14 and the second characteristic substance 16 from the synthesized luminance image 38 formed in the synthesized luminance image display step (Step S51), in the case where it is judged that two characteristic substances are present in the characteristic substance presence judging step (Step S42), and the extracted overlapping region is distinguishably displayed on the synthesized luminance image 38.

In this way, respective region information pieces of the luminance images of the characteristic substances can be synthesized, and the overlapping region of the two characteristic substances can be extracted and presented to the observer. Consequently, a region that is presumed as the noticeable region 12 of the lesion or the like can be presented to the observer, and the finding of the noticeable region 12 by the observer can further be facilitated.

Additionally, the display step (Step S5) further includes the contrast increasing step (Step S54) to grasp the presence region of the characteristic substance in one luminance image having a contrast value higher than the predetermined contrast value, when it is judged in the characteristic substance presence judging step (Step S42) that the contrast value of either one of the first luminance image 30 and the second luminance image 32 is less than the predetermined contrast value, and to increase the contrast of the same region in the other luminance image.

Thus, on the luminance image where one characteristic substance is not present, contrast increase processing is performed only to the same region as the region on the luminance image where the other characteristic substance is present, so that it is possible to confirm that the one characteristic substance really is not present in the region.

Furthermore, the display step (Step S5) further includes the luminance image display step (Step S58) to display the first luminance image 30 and the second luminance image 32, when it is judged in the characteristic substance presence judging step (Step S42) that contrast values of both of the first luminance image 30 and the second luminance image 32 is less than a predetermined contrast value.

Additionally, the characteristic substance presence image forming step (Step S4) can further include a characteristic substance emphasizing image formation and display step to form a characteristic substance emphasizing image 42 to emphasize and display the overlapping region 40A of the characteristic substances so that the overlapping region of the characteristic substances can be easily distinguished from other regions on the image.

In addition, the process further includes luminance image data storage steps (Step S53 and Step S57) to store the first luminance image 30, the second luminance image 32, and the synthesized luminance image 38 in which the first luminance image and the second luminance image are synthesized, Consequently, it is possible to present the stored image to a person other than the observer who operates the endoscope so that the person can carry out judgment of the noticeable region 12 of the lesion or the like.

It is to be noted that the first characteristic substance 14 and the second characteristic substance 16 are suitably different kinds of dyes that are suitable for different use applications, respectively, and known, for example, as markers for cancers. For example, the first characteristic substance 14 is hemoglobin, which is the blood vessel emphasizing substance to emphasize the blood vessel closely related to the tumor, and the second characteristic substance 16 is indigo carmine, which is the structure emphasizing substance to emphasize the structure or the bit pattern of the cells.

Consequently, the employment of various kinds of markers for the cancers exhibits the effects to heighten the prevention of the cancer detection errors and the detection sensitivity.

Furthermore, the endoscope apparatus 44 according to the present embodiment includes the narrowband light selector 60 that selects the first narrowband light 24 and the second narrowband light 28 containing wavelengths at which absorbances are mutually different in the first characteristic substance 14 and the second characteristic substance 16 contained in the noticeable region 12 of the intended observation object, the irradiating section 90 that irradiates the first narrowband light 24 and the second narrowband light 28 as the illumination light IL to the observation object, the imaging section 56 that performs imaging by use of the reflected light RL of the first narrowband light 24 and the reflected light RL of the second narrowband light 28 from the observation object, the image processor 58 that forms the characteristic substance presence images indicating the presence of the first characteristic substance and the second characteristic substance on the basis of the imaging data obtained in the imaging section 56, and the image display 50 that displays the characteristic substance presence image.

Thus, the narrowband light are irradiated to the subject 10, for the characteristic substances 14, 16 closely related to the noticeable region 12 that is the intended observation object, the narrowband light having the wavelengths at which the absorbances are mutually different, so that the characteristic substances 14, 16 related to the noticeable region 12 can be detected, and as a result, it is possible to improve the discovery precision of the observation object.

Here, the narrowband light selector 60 includes the narrowband light wavelength selector 92 that selects, as the first narrowband light 24 and the second narrowband light 28, the narrowband light contained in the first wavelength range containing the wavelength at which the difference between the absorbance at every wavelength of the first characteristic substance 14 and the absorbance at every wavelength of the second characteristic substance 16 is the largest value or the maximum value, and the narrowband light contained in the second wavelength range containing the wavelength at which the above difference is the smallest value or the minimum value.

That is, when the narrowband light 24 and 28 are selected, one characteristic substance is not specified, but specifying the two characteristic substances 14, 16 is desired. Therefore, when peak wavelengths of the respective characteristic substances are simply selected, it is difficult to specify the characteristic substances in a case where the peak wavelengths are close to each other (in the same wavelength range). To eliminate the problem, the wavelength at which the difference between the absorbances is largest or maximum or smallest or minimum so that the two characteristic substances 14, 16 can be specified. The selection is not limited to the peak wavelength of each characteristic substance, and there exists a wavelength that is usable if these selection conditions are satisfied.

Alternatively, the narrowband light selector 60 can include the narrowband light wavelength selector 92 that selects, in the first characteristic substance 14 and the second characteristic substance 16, narrowband light having a wavelength at which an absorbance of one characteristic substance is ½ or less, suitably ⅕ or less, and further suitably ¹⁄₁₀ or less of that of the other characteristic substance, and narrowband light having a wavelength at which an absorbance of the other characteristic substance is ½ or less, suitably ⅕ or less, and further suitably ¹⁄₁₀ or less of that of the one characteristic substance, as the first narrowband light 24 and the second narrowband light 28, respectively.

That is, the wavelength at which the absorbances are excessively different (½ or less, suitably ⅕ or less, and further suitably ¹⁄₁₀ or less of that of the one characteristic substance) is selected, so that two characteristic substances can be specified.

Alternatively, the narrowband light selector 60 can include the narrowband light wavelength selector 92 that selects two kinds of narrowband light having the wavelengths at which the absorbances of the first characteristic substance 14 and the second characteristic substance 16 are mutually reversed, as the first narrowband light 24 and the second narrowband light 28.

That is, the wavelength at which the absorbances are reversed is selected, so that two characteristic substances can be specified.

Furthermore, in the endoscope apparatus according to the present embodiment, the image processor 58 includes the luminance image forming section 96 that forms, as the characteristic substance presence images, the first luminance image 30 of the image information indicating the presence of the first characteristic substance 14 and the second luminance image 32 of the image information indicating the presence of the second characteristic substance 16 on the basis of the luminance obtained from the imaging data, and the characteristic substance presence judging section 98 that judges the presence or absence of the characteristic substance from the luminance image contrast of each of the first luminance image 30 and the second luminance image 32.

As understood from the above, the presence or absence of the characteristic substance can easily be judged from the contrast in the luminance image.

Additionally, in this case, the image processor 58 further includes the synthesis luminance image forming section 100 that synthesizes two luminance images of the first luminance image 30 and the second luminance image 32 to form the synthesized luminance image 38, when it is judged that the two characteristic substances are present in the characteristic substance presence judging section 98, the overlapping region extracting section 102 that extracts only the overlapping region of the first characteristic substance 14 and the second characteristic substance 16 from the synthesized luminance image 38, and the distinction image forming section 104 that distinguishably displays the extracted overlapping region on the synthesized luminance image 38.

In this way, the respective region information pieces of the luminance images of the characteristic substances can be synthesized, and the overlapping region of the two characteristic substances can be extracted and presented to the observer. Consequently, the region that is presumed as the noticeable region 12 of the lesion or the like can be presented to the observer, and the finding of the noticeable region 12 by the observer can further be facilitated. Additionally, the image processor 58 further includes the contrast increasing section 106 that, when it is judged in the characteristic substance presence judging section 98 that the contrast value of either one of the first luminance image 30 and the second luminance image 32 is less than the predetermined contrast value, grasps the presence region of the characteristic substance in the one luminance image having a contrast value higher than the predetermined contrast value or more, and increases the contrast in the same presence region in the other luminance image.

Thus, on the luminance image where one characteristic substance is not present, the contrast increase processing is performed only to the same region as the region on the luminance image where the other characteristic substance is present, so that it is possible to confirm that the one characteristic substance really is not present in the region.

The present invention has been described above on the basis of the embodiment, but the present invention is not limited to the above-mentioned embodiment, and needless to say, various modifications or applications are possible in the scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope observation method comprising:
   irradiating, to an observation object, first narrowband light and second narrowband light having wavelengths at which absorbances of a first characteristic substance and a second characteristic substance related to a predetermined state of the observation object and contained in the observation object are mutually different;
   performing imaging by use of reflected light of the first narrowband light from the observation object to obtain first image data, and by use of reflected light of the second narrowband light to obtain second image data; and
   forming a characteristic substance presence image regarding presence of the first characteristic substance and the second characteristic substance, on the basis of a characteristic amount of the first characteristic substance contained in the first image data and a characteristic amount of the second characteristic substance contained in the second image data,
   wherein the first characteristic substance and the second characteristic substance are different kinds of dyes suitable for different use applications.

2. The endoscope observation method according to claim 1, further comprising performing narrowband light selection to select the first narrowband light and the second narrowband light both including a wavelength at which a difference between and/or a ratio of absorbances of the first characteristic substance and the second characteristic substance is a predetermined value or more.

3. The endoscope observation method according to claim 2, wherein the performing the narrowband light selection comprises selecting narrowband light contained in a first wavelength range containing a wavelength at which a difference between an absorbance of the first characteristic substance and an absorbance of the second characteristic substance is a largest value or a maximum value, and narrowband light contained in a second wavelength range containing a wavelength at which the difference is a smallest value or a minimum value, as the first narrowband light and the second narrowband light.

4. The endoscope observation method according to claim 2, wherein the performing the narrowband light selection comprises, in the first characteristic substance and the second characteristic substance, selecting narrowband light having a wavelength at which an absorbance of one characteristic substance is ½ or less of an absorbance of the other characteristic substance, and narrowband light having a wavelength at which the absorbance of the other characteristic substance is ½ or less of the absorbance of the one characteristic substance, as the first narrowband light and the second narrowband light.

5. The endoscope observation method according to claim 2, wherein the performing the narrowband light selection further comprises:
    selecting the first characteristic substance and the second characteristic substance; and
    selecting the first narrowband light and the second narrowband light in accordance with the selected first characteristic substance and second characteristic substance.

6. The endoscope observation method according to claim 2, wherein the performing the narrowband light selection further comprises selecting an irradiation sequence that simultaneously, alternately, or independently irradiates the first narrowband light and the second narrowband light.

7. The endoscope observation method according to claim 6, wherein the selecting the irradiation sequence comprises selecting a first irradiation mode that stabilizes the irradiation sequence of the first narrowband light and the second narrowband light, and a second irradiation mode that can arbitrarily change the irradiation sequence of the first narrowband light and the second narrowband light.

8. The endoscope observation method according to claim 1, further comprising performing narrowband light selection to select each of the first narrowband light and the second narrowband light, on the basis of an absorbance at every wavelength of each of the first characteristic substance and the second characteristic substance,
    wherein the performing the narrowband light selection comprises selecting narrowband light contained in a third wavelength range containing a wavelength at which an absorbance at every wavelength of each of the first characteristic substance and the second characteristic substance is a largest value or a maximum value, and narrowband light contained in a fourth wavelength range containing a wavelength at which an absorbance at every wavelength of each of the characteristic substances is a smallest value or a minimum value, as the first narrowband light and the second narrowband light.

9. The endoscope observation method according to claim 1,
    wherein the forming the characteristic substance presence image comprises forming, as the characteristic substance presence image, a first luminance image as image information showing the presence of the first characteristic substance, and a second luminance image as image information showing the presence of the second characteristic substance, on the basis of a luminance obtained from the first image data and the second image data.

10. The endoscope observation method according to claim 9,
    wherein the forming the characteristic substance presence image further comprises judging presence or absence of the characteristic substance from a contrast in each of the first luminance image and the second luminance image,
    wherein the judging the presence or absence of the characteristic substance comprises selecting a value of the contrast arbitrarily or from previously prepared values for separate use applications, and
    wherein the forming the characteristic substance presence image further comprises synthesizing two luminance images of the first luminance image and the second luminance image to form a synthesized luminance image, and displaying the synthesized luminance image.

11. The endoscope observation method according to claim 10,
    wherein the displaying further comprises displaying the first luminance image and the second luminance image, when it is judged that contrast values of both of the first luminance image and the second luminance image are less than a predetermined contrast value by judging the presence or absence of the characteristic substances, and
    wherein the forming the characteristic substance presence image further comprises forming a characteristic substance emphasizing image to emphasize and display an overlapping region of the characteristic substances so that the overlapping region of the characteristic substance can be easily distinguished from other regions on the image.

* * * * *